United States Patent
Corbera-Arjona et al.

(10) Patent No.: US 6,372,746 B1
(45) Date of Patent: Apr. 16, 2002

(54) DERIVATIVES OF ACYL-PIPERAZINYL-PYRIMIDINES, PREPARATION THEREOF AND APPLICATION AS MEDICAMENTS

(75) Inventors: Jordi Corbera-Arjona; David Vaño-Domenech; Jordi Frigola-Constansa, all of Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 09/462,880

(22) PCT Filed: Jul. 21, 1998

(86) PCT No.: PCT/ES98/00212

§ 371 Date: Feb. 24, 2000

§ 102(e) Date: Feb. 24, 2000

(87) PCT Pub. No.: WO99/05121

PCT Pub. Date: Feb. 4, 1999

(30) Foreign Application Priority Data

Jul. 21, 1997 (ES) ............................................. 9701627

(51) Int. Cl.[7] ................... C07D 403/04; C07D 403/14; A61K 31/506; A61P 25/04; A61P 25/08
(52) U.S. Cl. ................................... 514/252.14; 544/295
(58) Field of Search ...................... 544/295; 514/252.14

(56) References Cited

U.S. PATENT DOCUMENTS 4,547,505 A    10/1985  Oepen et al. ................ 514/255
4,959,368 A  * 9/1990   Awaya et al. ................ 544/295

FOREIGN PATENT DOCUMENTS

| EP | 0115713 | 8/1984 |
|----|---------|--------|
| EP | 0382637 | 8/1990 |
| EP | 0497659 | 8/1992 |
| WO | 9414779 | 7/1994 |

* cited by examiner

Primary Examiner—Richard L. Raymond
Assistant Examiner—Venkataraman Balasubramanian
(74) Attorney, Agent, or Firm—Ladas & Parry

(57) ABSTRACT

The derivatives of acyl-piperazinyl-pyrimidines of general formula (I), where X is O or S; $R_1$ is alkoxy or trifluoromethyl; $R_2$ is alkyl, cycloalkyl, heterocycloalkyl, aryl, arylalkyl, heteroaryl, or heteroarylalkyl, show activity in the central nervous system. Compounds of general formula (I) in which X is O can be obtained by reacting a derivative of pyrimidine with a derivative of piperazine or by reacting a derivative of piperazinyl-pyrimidine with a carboxylic acid or a salt or derivative thereof. Compounds of general formula (I) in which X is S can be obtained by reacting (I) in which X is O with Lawesson's reagent or with phosphorous pentasulphide. The compounds (I) show sedative activity, anticonvulsant, sleep-inducing or general anaesthetic activity and can be applied in human or veterinary medicine

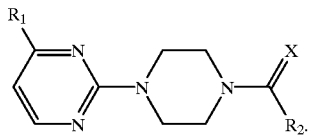

(I)

23 Claims, 1 Drawing Sheet

DERIVATIVES OF ACYL-PIPERAZINYL-PYRIMIDINES, PREPARATION THEREOF AND APPLICATION AS MEDICAMENTS

FIELD OF THE INVENTION

The present invention relates to new acyl-piperazinyl-pyrimidines of the general formula (I), to their physiologically acceptable salts, to procedures for their preparation, to their application as medicaments in therapy for humans and/or as veterinary medicaments and to the pharmaceutical compositions which contain said compounds.

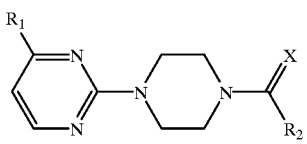

(I)

The new compounds object of the present invention can be used in the pharmaceutical industry as intermediates and for the preparation of medicaments.

BACKGROUND OF THE INVENTION

In our patents EP 382 637 and EP 497 659 we have described different derivatives of alkyl-piperazinyl-pyrimidines of the general formula (II) with ansiolytic and or tranquillising properties.

(II)

European patent EP-0 115 713 refers to (piperazinyl-1)-2-pirimidines, with substituents in position 4 of piperazine, consisting of an alkylcarbonyl group, alkylcarbonyl substituted by an amino or substituted amino group, an alkylcarboxylic or alkylcarboxylate group, or a substituted carbonylalkyl group, having psycotropic activity by means of a dopaminergic mechanism.

PCT application WO 94/14779, refers to (piperazinyl-1)-4-pirimidines, with substituents in position 4 of piperazine, only consisting of linear or branched alkyl chains of up to 4 carbon atoms, optionally terminating with a phenyl group which may be substituted, having antagonist activity of the 5-HT1 receptor and which may be used in the treatment or prevention of upsets related to excessive vasodilatation;

U.S. Pat. No. 4,547,505 patent refers to new pharmacologically active compounds, whose general formulation includes a piperazine, where one of the nitrogen atoms is substituted by groups, namely pyrimidine or others, and the other nitrogen atom is replaced by a substituted acyl group, and which possesses analgesic activity.

We have now discovered that the addition of a substituent to position 4 of the pyrimide and the substitution of an alkyl radical with an acyl radical gives rise to the new compounds of general formula (I). Said compounds show useful biological properties which makes them especially useful for their use in therapy in humans and veterinary therapy. The compounds of the present invention are useful as agents which act on the central nervous system in mammals including humans. In particular, the new compounds are useful as sedatives, anti-convulsants, sleep-inducing agents and general anaesthetics.

DETAILED DESCRIPTION OF THE INVENTION

Figure 1:
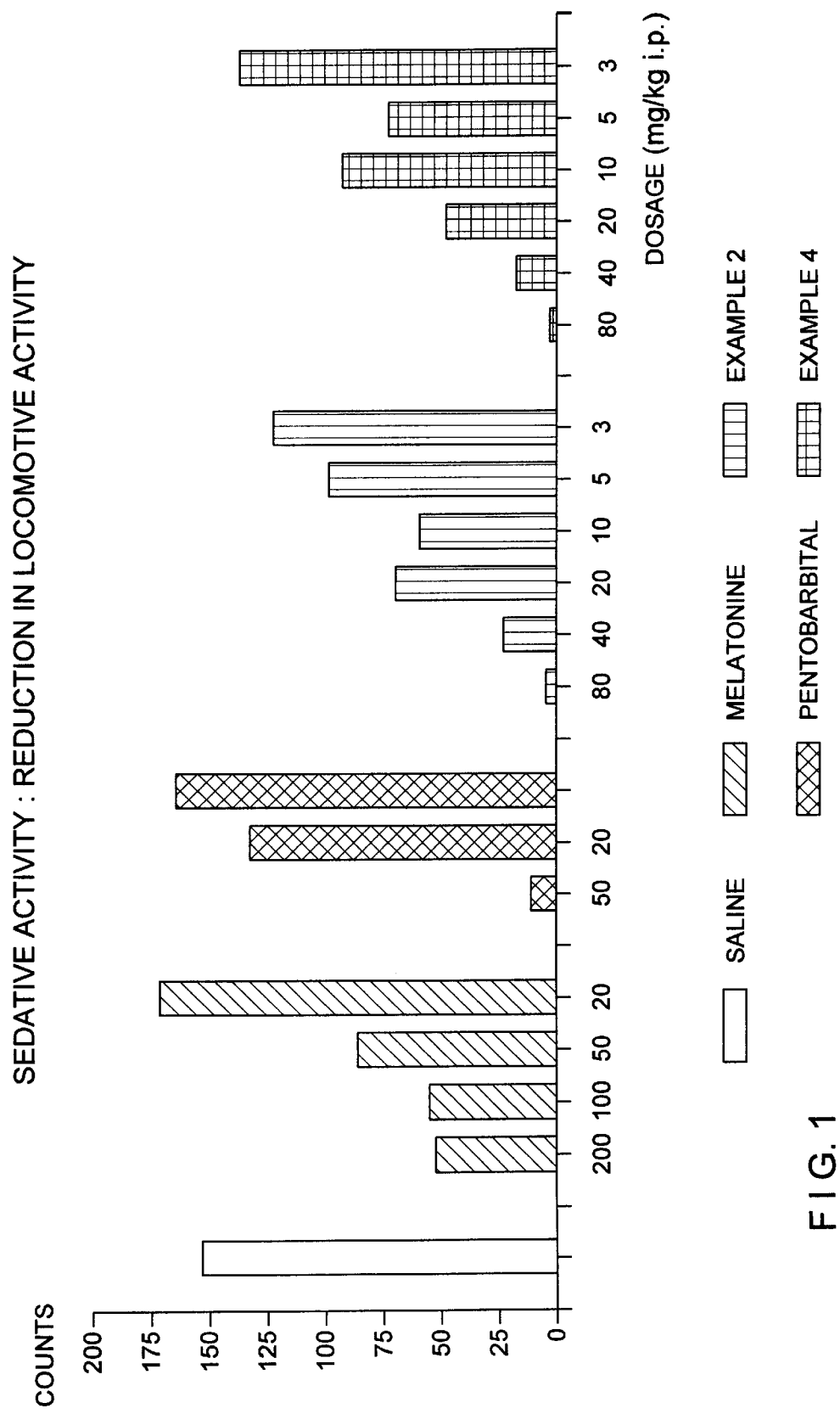
FIG. 1 shows the results of the sedative activity of some of the compounds of the invention, as determined by reduction in locomotive activity.

The present invention provides new compounds capable of inducing conscious sedation, of acting as sleep-inducing agents, anti-convulsants, analgesics, muscular relaxants, anti-tusigenics, ansiolytics, anti-psychotics, anti-depressants, anti-cerebral ischeamics, anti-migraine agents, agents useful for sleep disorders, agents for neurodegenerative diseases, agents for cognitive disorders and Alzheimer's disease, and agents capable of inducing or maintaining general anaesthesia, when administered by an appropriate method at a suitable dosage level.

The compounds of the present invention are represented by the general formula (I)

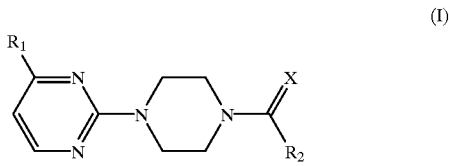

(I)

where

X is an oxygen or sulphur atom;

$R_1$ is a $C_{1-4}$ alkoxy or trifluoromethyl radical;

$R_2$ is a $C_{1-6}$ alkyl radical; $C_{3-6}$ saturated cycloalkyl; heterocycloalkyl consisting of a ring of 3 to 6 atoms in which the heteroatom is selected from an atom of oxygen, sulphur or nitrogen, optionally N-substituted with $C_1$–$C_6$ alkyl; phenyl optionally substituted with 1, 2 or 3 identical or different substituents selected from fluorine, chlorine, bromine, amino, acetamido, nitro, methyl, trifluoromethyl and methoxy; arylalkyl consisting of a $C_{1-3}$ alkyl group substituted by a phenyl radical optionally substituted by 1, 2 or 3 identical or different substituents selected from fluorine, chlorine, bromo, amino, acetamido, nitro, methyl, trifluoromethyl and methoxy; heteroaryl consisting of a 5 or 6 heteroatom ring, optionally substituted, or of fused heteroaromatic systems optionally substituted, of 9 or 10 atoms consisting of 1 or 2 heteroatoms selected from oxygen, sulphur and nitrogen, selecting the aforementioned substituents from flourine, chlorine, bromine, amino, acetamido, nitro, methyl, trifluoromethyl and methoxy; and heteroarylalkyl consisting of an alkyl group of 1 to 3 carbon atmos substituted with a heteroaryl radical consisting of a 5 or 6 member heteroaromatic ring, optionally substituted, or of fused 9 to 10 member heteroaromatic systems, optionally substituted with 1 or 2 heteroatoms selected from oxygen, sulphur and nitrogen, selected the aforementioned substituents from fluorine, chlorine, bromine, amino, acetamido, nitro, methyl, trifluoromethyl and methoxy; and their physiologically acceptable salts.

In the present invention, the term $C_{1-4}$ "alkoxy" represents a radical $OR_3$ in which $R_3$ is a saturated linear or branched carbon chain containing 1 to 4 atoms, such as methoxy, ethoxy, propoxy, isopropoxy, butoxy, sec-butoxy o tert-butoxy for example.

The term "alkyl" represents a radical derived from a saturated linear or branched hydrocarbon. The term $C_{1-6}$ alkyl represents a linear or branched chain alkyl radical containing 1 to 6 atoms of carbon, such as methyl, ethyl, propyl, isopropyl, butyl, isobutyl, sec-butyl, tert-butyl, pentyl, isopentyl, neopentyl and hexyl for example.

The term $C_{3-6}$ saturated "cycloalkyl" represents a saturated ring of 3 to 6 atoms of carbon, such as cyclopropyl, cyclobutyl, cyclopentyl or cyclohexyl for example.

The term "heterocycloalkyl" represents a ring of 3 to 6 atoms of which there is a heteroatom such as an oxygen atom or an atom of sulphur, such as a 2-aziridinyl, 2-tetrahydrofuryl, 3-tetrahydrofuryl, 2-tetrahydrothienyl, 3-tetrahydrothienyl for example, or an atom of nitrogen which may or may not be substituted, such as 2-azetidinyl, 2-piperidinyl, 3-piperidinyl or 4-piperidinyl for example.

The term "aryl" represents an unsubstituted or substituted phenyl radical, with 1, 2 or 3 identical or different substituents such as fluorine, chlorine, bromine, amino, acetamido, nitro, methyl, triflouromethyl or methoxy, such as 2-fluorophenyl, 3-fluorophenyl, 4-fluorophenyl, 2-chlorophenyl, 3-chlorophenyl, 4-chlorophenyl, 2-bromophenyl, 3-bromorophenyl, 4-bromophenyl, 2-aminophenyl, 3-aminophenyl, 4-aminophenyl, 2-nitrophenyl, 3-nitrophenyl, 4-nitophenyl, 2-acetamidophenyl, 3-acetamidophenyl, 4-acetamidophenyl, 2-nitrophenyl, 3-nitrophenyl, 4-nitrophenyl, 2-methylphenyl, 3-methylphenyl, 4-methylphenyl, 2-(trifluoromethyl)phenyl, 3-(trifluoromethyl)phenyl, 4-(trifluoromethyl)phenyl, 2-metoxyphenyl, 3-metoxyphenyl, 4-metoxyphenyl, 2,3-difluorophenyl, 3,4-difluorophenyl, 2,4-difluorophenyl, 2,3-dibromophenyl, 3,4-dibromophenyl, 2,4-dibromophenyl, 2,3-dimethylphenyl, 3,4-dimethylphenyl, 2,4-dimnethylphenyl, 2,3-dimethoxyphenyl, 3,4-dimethoxyplenyl, 2,4-dimethoxyphenyl for example.

The term "arylalkyl" represents a linear or branched chain of 1 to 3 atoms of carbon which is substituted with an aryl radical, according to the hereinbefore definition of "aryl", and which includes substituents such as phenylmethyl, 1-phenylethyl, 2-phenylethyl, 3-phenylethyl, 3-phenylpropyl, as well as other radicals in which the aromatic ring is substituted with groups such as fluorine, chlorine, bromine, amino, acetamido, nitro, methyl, trifluoromethyl or methoxy.

The term "theteroaryl" represents a substituted or unsubstituted heteraromatic ring of 5 or 6 members or unsubstituted or substituted fused heteroaromatic systems of 9 or 10 members consisting of 1 or 2 heteroatoms such as nitrogen, oxygen or sulphur, with the substituent groups being groups such as fluorine, chlorine, bromine, amino, acetamido, nitro, methyl, trifluoromethyl or methoxy, such as 2-furyl, 3-fluryl, 2-thienyl, 3-thienyl, 3-methyl-2-thienyl, 5-methyl-2-thienyl, 3-methoxy-2-thienyl, 3-chloro-2-thienyl, 5-chloro-2-thienyl, 2-pyrrolyl, 3-pyrrolyl, 2-pyridyl, 3-pyridyl, 4-pyridyl, 2-indolyl, 3-indolyl, 2-benzo[b]thienyl, 3-benzyo[b]thienyl, 3-chloro-2-benzo[b]thienyl, pirazolyl, imidazolyl, pyrimidinyl, piridazinyl, pirazinyl, benzimidazolyl, quinolyl, oxazolyl and thiazolyl for example.

The term "heteroarylalyl" represents an alkyl group of 1 to 3 atoms of carbon which is substituted with a heteroaryl radical, according to the hereinbefore definition of "heteroaryl", and which includes substituents such as 2-thienymethyl, 2-benzo[b]thienylmethyl and 3-(4-chloropyrazolyl)propyl.

The new compounds of general formula (I) may contain an asymmetric carbon atom and can therefore be prepared as optical isomers or racemates. The racemates of compounds (I) can be resolved into their optical isomers using conventional methods, such as separation by chiral chromatography or fractionated crystallisation from their diastereoisomer salts for example. Similarly, they can also be obtained from asymmetric synthesis using chiral precursors.

The present invention also relates to physiologically acceptable salts of the compounds of general formula (I), in particular addition salts of mineral acids such as hydrochloric acid, hydrobromic acid, phosphoric acid, sulphuric acid, nitric acid and addition salts of organic acids such as p-toluensulphonic acid or methansulphonic acid.

The new derivatives of general formula (I), in which X is an atom of oxygen and $R_1$ and $R_2$ have the hereinbefore defined meaning, can be prepared according to methods A or B which are described below.

METHOD A

The compounds of general formula (I) can be prepared by reacting the derivative of chloropyrimidine (D), where $R_1$ has the hereinbefore defined meaning, with a derivative of piperazine of general formula (IV) in which X and $R_2$ have the hereinbefore defined meaning.

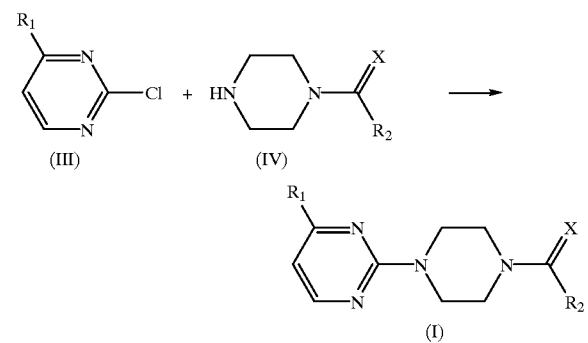

The reaction is carried out in an organic solvent, for example in an chlorinated hydrocarbon such as dichloromethane or chloroform, a linear or cyclic ether such as 1,2-dimethoxyethane, tetrahydrofurane or dioxane, a aprotic polar solvent such as pyridine, dimethylsulphoxide or dimethylformamide or any other type of solvent appropriate for carry out a aromatic nucleophilic substitution reaction. The reaction can be carried out in the presence of a mineral or organic base such as an aliphatic amine, preferably triethylamine or M-methylmorphine by stirring at a temperature lying between room temperature and the boiling point of the solvent for a period of time lying between ten minutes and twenty-four hours, the preferring conditions being a period of time between thirty minutes and five hours.

METHOD B

By Reaction of the Amine of Formula (V):

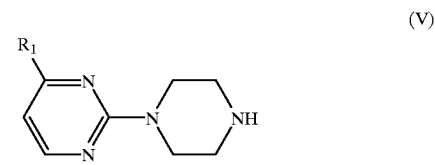

in which $R_1$ has the hereinbefore defined meaning with a carboxylic acid of the general formula $R_2COOH$ (VI), in which $R_2$ has the hereinbefore defined meaning, or with a salt of said acid or also with a derivative reagent $R_2COY$ (VII).

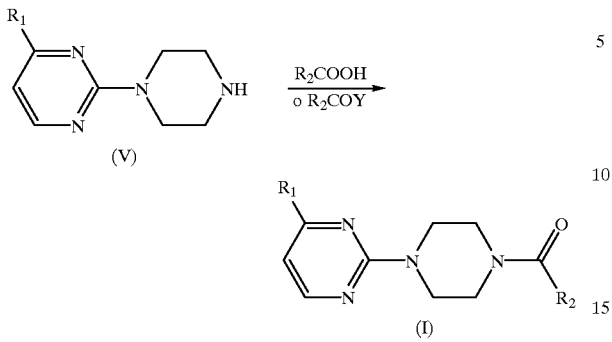

Examples of salts include salts of alkali metals such as sodium salts and potassium salts, alkaline earth salts such as calcium salts and magnesium salts, ammonium salts, and salts of organic bases such as triethylamine, trimethylamine, pyridine and picoline.

Examples of derivative reagents of general formula $R_2COY$ (VII) in which Y is a halogen atom preferably a chlorine atom or a bromine atom, an azide group (—$N_3$), a 1-imidazolyl, a O—CO—$R_4$, in which $R_4$ can be an alkyl or aryl radical of 1 to 6 carbon atoms, preferably substituted with one or several halogen atoms, or a group $OR_5$ where $R_5$ represents an aromatic group of one or two rings substituted with one or several halogen atoms or nitro radicals, the preferred groups being 4-nitrophenyl, 2,4-dinitrophenyl, pentachlorophenyl, pentafluorophenyl, 1-benzotriazolyl o N-succinimide. Similarly, instead of using the aforementioned derivative reagents, compounds of general formula (I) can be prepared directly by reaction of the amine (V) with the carboxylic acid or general formula (VI). In this case it is preferable that the reaction proceeds in the presence of reagents that activate the carbonyl groups such as N,N'-dicyclohexylcarbodiimide, diisopropylcarbondiimide or 3-(3-dimethylamino)propyl-1-ethycarbodiimide. This reaction can also be carried out using the said carbodiimidas in the presence of 1-benzotriazol or N-hydroxysuccinimide The acids of general formula (VI) and the amine of formula (V) also react directly in the presence of N,N'-carbonyldiimidazol or of propanophosphonic acid anhydride.

The reaction is carried out in an organic solvent, for example in an chlorinated hydrocarbon such as dichloromethane or chloroform, a linear or cyclic ether such as 1,2-dimethoxyethane, tetrahydrofurane or dioxane, a aprotic polar solvent such as pyridine, dimethylsulphoxide or dimethylformamide or any other type of solvent appropriate for carry out a aromatic nucleophilic substitution reaction. The reaction can be carried out in the presence of a mineral or organic base such as an aliphatic amine, preferably tnrethylamine or M-methylmorphine by stirring at a temperature lying between room temperature and the boiling point of the solvent for a period of time lying between ten minutes and twenty-four hours, the preferring conditions being a period of time between thirty minutes and five hours.

METHOD C

The new derivatives of general formula (I), in which X is an atom of sulphur and $R_1$ and $R_2$ have the hereinbefore defined meaning, can be prepared according to the following method.

By treating a compound of a compound of general formula (I), in which $R_1$ and $R_2$ have the hereinbefore defined meaning and in which X is an atom of oxygen, with Lawesson's reagent (2,4-bis(4-methoxyphenyl)-1,3,2,4-dithiadiphosphaethano-2,4-disulphuro) or with phosphorous pentasulphide, the corresponding thioamides are obtained in which X is a sulphur atom:

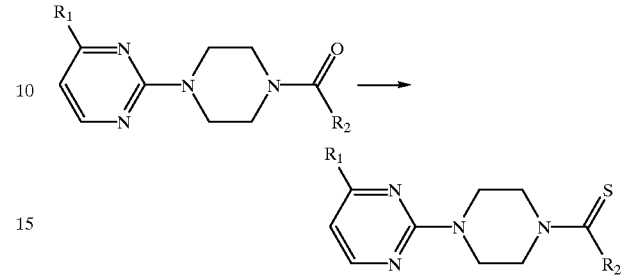

The reaction is carried out in an organic solvent such as toluene, benzene, heptane, pyridine or tetrahydrofurane. The reaction is continually shaken at a temperature lying between room temperature and the boiling point of the solvent for a period of time of between one hour and twenty-four hours, preferably carrying out the reaction at 80° C. for a time between one hour and sixteen hours.

METHOD D

The salts of the compounds of general formula (I) can be prepared by reaction with a mineral acid such as hydrochloric acid, hydrobromic acid, phosphoric acid, sulphuric acid, nitric acid or with an organic acid such as p-toluensulphonic acid or methansulphonic acid in an appropriate solvent such as methanol, ethanol, ethyl ether, ethyl acetate, acetonitrile or acetone, being obtained with the normal precipitation techniques or crystallisation of the corresponding salts.

The invention provides pharmaceutical compositions which comprise, as well as a pharmaceutically acceptable excipient, at least one compound of general formula (I) or one of their physiologically acceptable salts. The invention also relates to the use of a compound of general formula (I) and their physiologically acceptable salts in the elaboration of a medicament with activity in the mammalian, central nervous system, including activity in the human central nervous system in particular, in the manufacture of a medicament with sedative, anticonvulsive, sleep-inducing and general anaesthetic activity.

In the examples which follow the preparation of new compounds according to the invention is indicated. Also described are some typical forms of use for the different fields of application, as well as medicinal formulas applicable to the compounds of the invention.

METHOD A

EXAMPLE 1

Preparation of 2-[4-(2-furylcarbonyl-1-piperazinyl]-4-methoxy-pyrimidine

A solution of 1.0 g (6.92 mmol) of 2-chloro-4-methoxypyrimidine, 1.49 g (8,30 mmol) of 1-(2-furylcarbonyl)piperazine and 1.39 g (13.84 mmol) of triethylamine in 20 mL of n-butanol is maintained under gentle reflux conditions overnight. The solvent is evaporated off under reduced pressure and the crude residue is diluted in chloroform and washed in water. The organic phase is dried over $NaSO_4$ and evaporated to dryness to give a crude product which is purified using silica-gel chromatography eluting with ethyl acetate/petroleum ether 70:30 to yield an oil which solidifies when left to stand. The solid is suspended in petroleum ether to yield 1.4 g (4.86 mmol) of 2-[4-(2-furylcarbonyl)-1-piperazinyl]-4-methoxypyrimidine. m.p.=85–86° C.

METHOD B

EXAMPLE 3

Preparation of 4-methoxy-2-4-(2-thienylcarbonyl)-1-piperazinyl]pyrimidine

A solution of 1.0 g (5.15 mmol) of 4-methoxy-2-(1-piperazinyl)pyrimidine and 1 mL (7.18 mmol) of triethylamine in 30 mL of $CH_2Cl_2$ is cooled to 0° C. and 0.76 g (5.18 mmol) of 2-thienylcarbonyl chloride slowly added. The solution is kept at 0° C. for an hour and then the temperature allowed to rise to room temperature. The organic phase is washed with $H_2O$, dried over $NaSO_4$ and the solvent removed under reduced pressure. The crude residue is dissolved in ethyl ether crystallising 1.0 g (3.28 mmol) of 4-methoxy-2-[4-(2-thiencarbonyl)-1-piperazinyl] pryimidine. m.p.=71–73° C.

EXAMPLE 12

Preparation of 4-methoxy-2-[4-(3-thienylcarbonyl)-1-piperazinyl]pyrimidine

To a solution of 1.0 g (7.81 mmol) of 3-thienylcarboxylic acid and 1 mL (7.86 mmol) of triethylamine in 30 mL of $CH_2Cl_2$ cooled to 0° C. 0.84 g (7.81 mmol) of ethyl chloroformiate are added. The mixture is maintained at 0° C. for 20 minutes and then 1.5 g (7.81 mmol) of 4-methoxy-2-(1-piperazinyl) pyrimidine dissolved in 10 mL of $CH_2Cl_2$ are added to the solution. The temperature is allowed to rise to room temperature and the solution continually stirred for 2 hours and the organic phase is washed with $H_2O$, dried over $NaSO_4$ and the solvent evaporated off under reduced pressure. The resulting oil is treated with ethyl ether to yield a solid which is recrystallised from ethanol/$H_2O$ to give 0.8 g (2.63 mmol) of 4-methoxy-2-[4-(3-thienylcarbonyl)-1-piperazinyl]pyrimidine. m.p.=90–92° C.

EXAMPLE 20

Preparation of 2-[4-(2-inolylcarbonyl)-1-piperazinyl]-4-methoxy pyrimidine

To a solution of 0.83 g (5.15 mmol) of indol-2-carboxylic acid in 15 mL of dry THF 0.83 g (5.15 mmol) of N,N'-carbonyldiimidazol is added. After 30 minutes 1.0 g (5.15 mmol) of 4 methoxy-2-(1-piperazinyl) pyrimidine is added to the solution and it is left overnight with continuous stirring. The solvent is eliminated under reduced pressure and $H_2O$ added. This produces a precipitate which is filtered and dried, to give 1.7 g (5.04 mmol) of 2-[4-(2-indolylcarbonyl)-1-piperazinyl]-4-methoxypyrimidine. m.p.=202–203° C.

METHOD C

EXAMPLE 54

Preparation of 4-methoxy-2-(4-thiobenzoyl-1-piperazinyl)pyrimidine 0.56 g (1.9 mmol) of 2-(4-benzoyl-1-piperazinyl)-4-methoxypyrimidine are dissolved in 25 mL of dry toluene, and 0.46 g (1.14 mmol) of Lawesson's reagent (2,4-bis(4-methoxyphenyl)-1,32,4-dithiadiphosphaethano-2,4-disulphide) added. The mixture is heated to 80–90° C. for 16 hours. Ethyl ether is added, basic water is used to wash the residue and the organic extract is dried with $NaSO_4$ and the solvent evaporated off under reduced pressure. The resulting crude residue is crystallised with ethyl ether-petroleum ether to give 160 mg (0.5 mmol) of 2-(4-thiobenzoyl-1-piperazinyl)-4-methoxypyrimidine. m.p.=125–129° C.

METHOD D

EXAMPLE 2

Preparation of 2-[4-(2-furylcarbonyl)-1-piperazinyl]-4-methoxypyrimidine chlorohydrate 1.0 g (3.47 mmol) of 2-[4-(2-furylcarbonyl)-1-piperazinyl]-4-methoxypyrimidine in ethyl acetate and a few drops of a solution of ethyl ether/hydrochloric acid are added, thus obtaining a precipitate which is filtered and dried, to yield 1.07 g (3.29 mmol) of 2-[4-(2-furylcarbonyl)-1-piperazinyl]-4-methoxypyrimidine chlorohydrate. m.p.= 162–164° C.

EXAMPLE 4

Preparation of 4-methoxy-2-[4-2-thienylcarbonyl)-1-piperazinyl]pyrimidine chlorohydrate.

1.0 g (3.29 mmol) of 4methoxy-2-[4-(2-thienylcarbonyl)-1-piperazinyl]pyrimidine is dissolved in acetone and a few drops of a solution of ethyl ether/hydrochloric acid are added, thus obtaining a precipitate which is filtered and dried, to yield 1.05 g (3.08 mmol) of 4-methoxy-2-[4-(2-thienylcarbonyl)-1-piperazinyl]pyrimidine chlorohydrate. m.p.=143–145° C.

EXAMPLE 13

Preparation of 4-methoxy-2-[4-(3-thienylcarbonyl)-1-piperazinyl]pyrimidine chlorohydrate 0.8 g (2.63 mmol) of 4-methoxy-2-[4-(3-thienylcarbonyl)-1-piperazinyl]pyrimidine is dissolved in ethanol and a few drops of a solution of ethanol/hydrochloric acid are added, thus obtaining a precipitate which is filtered and dried, to yield 0.6 g (1.76 mmol) of 4-methoxy-2-[4-(3-thienylcarbonyl)-1-piperazinyl] pyrimidine chlorohydrate. m.p.154–156° C.

TABLE 1

[Structure: pyrimidine with R¹ at 4-position, connected at 2-position to piperazine, other piperazine N connected to C(=X)R₂]

| Example | R₁ | R₂ | X | Base or Salt | Procedure | m.p. (°C.) | ¹H RMN (MHz) (Solvent) δ | IR, cm⁻¹ |
|---|---|---|---|---|---|---|---|---|
| 1 | CH₃O— | 2-furyl | O | base | A | 85–86 | (300 MHz) (CDCl₃) 3.90 (broad singlet, 11H), 6.04(d, J=5.5Hz, 1H), 6.51(dd, J=3.5Hz, J'=1.7Hz, 1H), 7.05(d, J=3.5Hz, 1H), 7.51(broad singlet, 1H), 8.07(d, J=5.5Hz, 1H). | (KBr) 1623, 1598, 1583, 1561, 1502, 1439, 1264, 1025. |
| 2 | CH₃O— | 2-furyl | O | HCl | D | 162–164 | (300 MHz) (DMSO-d₆) 3.83 (m, 4H), 3.91(m, 4H), 3.95(s, 3H), 6.36(d, J=6.3Hz, 1H), 6.66(m, 1H), 7.07(m, 1H), 7.88(m, 1H), 8.16(d, J=6.3Hz, 1H). | (KBr) 2800–2200 (broad), 1642, 1605, 1483, 1262. |
| 3 | CH₃O— | 2-thienyl | O | base | B | 71–73 | (300 MHz) (CDCl₃) 3.83 (m, 4H), 3.89(a.c., 7H, (δ=3.89, s)), 6.04(d, J=5.7Hz, 1H), 7.07(dd, J=5.1Hz, J'=3.9Hz, 1H), 7.33(d, J=3.9Hz, 1H), 7.48(d, J=5.1Hz, 1H), 8.07(d, J=5.7Hz, 1H). | (KBr) 1598, 1561, 1432, 1257, 989. |
| 4 | CH₃O— | 2-thienyl | O | HCl | D | 143–145 | (300 Mhz) (DMSO-d₆) 3.80 (m, 4H), 3.91(m, 4H), 3.95(s, 3H), 6.37(d, J=6.5Hz, 1H), 7.15(dd, J=4.9Hz, J'=3.6Hz, 1H), 7.49(dd, J=3.6Hz, J'=1.2Hz, 1H), 7.80 (dd, J=4.9Hz, J'=1.2Hz, 1H), 8.15(d, J=6.5Hz, 1H). | (KBr) 2800–2200 (broad), 1637, 1614, 1597, 1484, 1437, 1409, 1210. |
| 5 | CH₃O— | CH₃ | O | base | A | 119–120 | (300 MHz) (CDCl₃) 2.15 (s, 3H), 3.52(m, 2H), 3.68(m, 2H), 3.83(m, 4H), 3.89(s, 3H), 6.02(d, J=5.7Hz, 1H), 8.06(d, J=5.7Hz, 1H). | (KBr) 1654, 1595, 1561, 1423, 1345, 1249, 988. |
| 6 | CH₃O— | 4-chloro-1H-pyrazol-1-yl-(CH₂)₃— | O | base | B | aceite | (330 MHz) (CDCl₃) 2.21 (m, 2H), 2.32(m, 2H), 3.45 (m, 2H), 3.68(m, 2H), 3.80 (m, 4H), 3.89(s, 3H), 4.20(t, J=6.5Hz, 2H), 6.03(d, J=5.7 Hz, 1H), 7.40(s, 1H), 7.42(s, 1H), 8.05(d, J=5.7Hz, 1H). | (film) 1651, 1644, 1588, 1470, 1339. |
| 7 | CH₃O— | 4-chloro-1H-pyrazol-1-yl-(CH₂)₃— | O | HCl | D | 148–149 | (300 MHz) (DMSO-d₆) 1.98 (q, J=6.9Hz, 2H), 2.33(t, J=7.0Hz, 2H), 3.57(m, 4H), 3.82(m, 4H), 3.95(s, 3H), 4.10(t, J=6.9Hz, 2H), 6.36 (d, J=6.6Hz, 1H), 7.50(s, 1H), 7.98(s, 1H), 8.14(d, J=6.6Hz, 1H). | (KBr) 2800–2200 (broad), 1641, 1610, 1484, 1437, 1353, 1270, 1216. |
| 8 | CH₃O— | phenyl | O | base | B | 99–102 | (300 MHz) (CDCl₃) 3.52 (m, 2H), 3.73–4.00(a.c., 9H, (δ=3.88, s)), 6.03(d, J=5.5Hz, 1H), 7.44(s, 5H), 8.06 (d, J=5.5Hz, 1H). | (KBr) 1625, 1606, 1597, 1558, 1461, 1428, 1266, 988. |
| 9 | CH₃O— | cyclopropyl | O | base | B | 76–78 | (300 MHz) (CDCl₃) 0.80 (m, 2H), 1.02(m, 2H), 1.78 (m, 1H), 3.68–3.92(a.c., 11H, (δ=3.89, s)), 6.02(d, J=5.7Hz, 1H), 8.06(d, J=5.7 Hz, 1H). | (KBr) 1638, 1589, 1567, 1470, 1444, 1335, 1235, 1225. |

TABLE 1-continued

| Example | R₁ | R₂ | X | Base or Salt | Procedure | m.p. (° C.) | $^1$H RMN (MHz) (Solvent) δ | IR, cm$^{-1}$ |
|---|---|---|---|---|---|---|---|---|
| 10 | CF$_3$— | 2-furyl | O | base | A | 112–113 | (300 MHz) (CDCl$_3$) 3.84–4.00(a.c., 8H), 6.51(dd, J=3.5 Hz, J'=1.7Hz, 1H), 6.82(d, J=4.8Hz, 1H), 7.06(dd, J=3.5 Hz, J'=1.0Hz, 1H), 7.51(dd, J=1.7Hz, J'=1.0Hz, 1H), 8.51(d, J=4.8Hz, 1H). | (KBr) 1620, 1592, 1509, 1332, 1268, 1138. |
| 11 | CF$_3$— | 2-thienyl | O | base | B | 136–137 | (300 MHz) (CDCl$_3$) 3.86 (a.c., 4H), 3.96(a.c., 4H), 6.82(d, J=4.8Hz, 1H), 7.08 (dd, J=5.0Hz, J'=3.7Hz, 1H), 7.34(dd, J=3.7Hz, J'=1.1Hz, 1H), 7.48(dd, J=5.0Hz, J'=1.1Hz, 1H), 8.52(d, J=4.8Hz, 1H). | (KBr) 1594, 1521, 1430, 1336, 1262, 1151. |
| 12 | CH$_3$O— | 3-methylthienyl | O | base | B | 90–92 | (300 MHz) (CDCl$_3$) 3.72 (m, 4H), 3.80–3.96(a.c., 7H, (δ=3.89, s)), 6.03(d, J=5.6Hz, 1H), 7.22(d, J=5.0Hz, 1H), 7.36(m, 1H), 7.56(broad singlet, 1H), 8.06(d, J=5.6Hz, 1H). | (KBr) 1623, 1595, 1582, 1561. |
| 13 | CH$_3$O— | 3-methylthienyl | O | HCl | D | 154–156 | (300 MHz) (DMSO-d$_6$) 3.66 (m, 4H), 3.87(m, 4H), 3.92(s, 3H), 6.32(d, J=6.1Hz, 1H), 7.24(m, 1H), 7.63(broad singlet, 1H), 7.85(broad singlet, 1H), 8.14(d, J=6.1Hz, 1H). | (KBr) 2800–2200 (broad), 1642, 1617, 1598. |
| 14 | CH$_3$O— | 2,5-dimethylthienyl | O | base | B | 90–92 | (300 MHz) (CDCl$_3$) 2.51 (s, 3H), 3.79–3.93(a.c., 11H, (δ=3.89, s)), 6.03(d, J=5.6Hz, 1H), 6.72(m, 1H), 7.15(d, J=3.5Hz, 1H), 8.06 (d, J=5.6Hz, 1H). | (KBr) 1625, 1590, 1562, 1510, 1471, 1414, 1261. |
| 15 | CH$_3$O— | 2,5-dimethylthienyl | O | HCl | D | 115–119 | (300 Mhz) (CDCl$_3$) 2.46 (s, 3H), 3.79(m, 4H), 3.91(m, 4H), 3.95(s, 3H), 6.37(d, J=6.4Hz, 1H), 6.84(m, J=3.6Hz, 1H), 7.29(d, J=3.6Hz, 1H), 8.14(d, J=6.4Hz, 1H). | (KBr) 2800–2200 (broad), 1641, 1615, 1602, 1488, 1412, 1260. |
| 16 | CH$_3$O— | 2-methyl-3-methoxythienyl | O | base | B | 99–101 | (300 MHz) (CDCl$_3$) 3.69 (a.c., 4H), 3.85–3.93(a.c., 10H, (δ=3.90, two singlets)), 6.02(d, J=5.7Hz, 1H), 6.80 (d, J=5.6HZ, 1H), 7.37(d, J=5.6Hz, 1H), 8.07(d, J=5.7Hz, 1H). | (KBr) 1623, 1594, 1656. |
| 17 | CH$_3$O— | 2-methyl-3-methoxythienyl | O | HCl | D | 162–165 | (300 MHz) (DMSO-d$_6$) 3.60 (a.c., 4H), 3.82–3.90(a.c., 7H, (δ=3.88, s)), 3.94(s, 3H), 6.33(d, J=6.3Hz, 1H), 7.04(d, J=5.6Hz, 1H), 7.69 (d, J=5.6Hz, 1H), 8.14(d, J=6.3Hz, 1H). | (KBr) 2800–2200 (broad), 1640, 1610, 1479, 1442, 1406. |

TABLE 1-continued

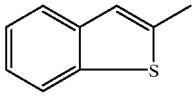

| Example | R₁ | R₂ | X | Base or Salt | Procedure | m.p. (° C.) | ¹H RMN (MHz) (Solvent) δ | IR, cm⁻¹ |
|---|---|---|---|---|---|---|---|---|
| 18 | $CH_3O-$ | 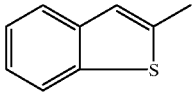 | O | base | B | 173–174 | (300 MHz) ($CDCl_3$) 3.86 (m, 4H), 3.90(s, 3H), 3.92(m, 4H), 6.05(d, J=5.7Hz, 1H), 7.42(a.c., 2H), 7.53(s, 1H), 7.85(a.c., 2H), 8.07(d, J=5.7 Hz, 1H). | (KBr) 1604, 1589, 1559, 1459, 1259, 991. |
| 19 | $CH_3O-$ | 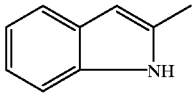 | O | HCl | D | 155–156 | (300 MHz) (DMSO-$d_6$) 3.84 (m, 4H), 3.89–3.97(a.c, 7H, (δ=3.93, s)), 6.32(d, J=6.3Hz, 1H), 7.45(a.c., 2H), 7.81(s, 1H), 7.94(m, 1H), 8.02(m, 1H), 8.15(d, J=6.3 Hz, 1H). | (KBr) 2800–2200 (broad), 1644, 1611, 1487. |
| 20 | $CH_3O-$ | 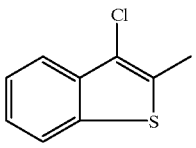 | O | base | B | 202–203 | (300 MHz) ($CDCl_3$) 3.92 (s, 3H), 3.93–4.10(a.c., 8H), 6.05(d, J=5.6Hz, 1H), 6.83 (d, J=1.4Hz, 1H), 7.15(t, J=7.3Hz, 1H), 7.30(t, J=7.3Hz, 1H), 7.45(d, J=8.3 Hz, 1H), 7.67(d, J=8.3Hz, 1H), 8.09(d, J=5.6Hz, 1H), 9.42(broad singlet, 1H). | (KBr) 3260, 1605, 1578, 1571, 1438, 1336, 1251. |
| 21 | $CH_3O-$ | 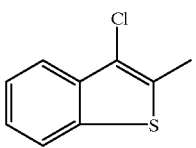 | O | base | B | 175–176 | (300 MHz) ($CDCl_3$) 3.59 (m, 2H), 3.88(s, 3H), 3.92(m, 6H), 6.04(d, J=5.6Hz, 1H), 7.50(a.c., 2H), 7.86(a.c., 2H) 8.06(d, J=5.6Hz, 1H). | (KBr) 1638, 1588, 1564, 1263. |
| 22 | $CH_3O-$ | 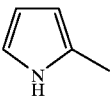 | O | HCl | D | 164–165 | (300 MHz) (DMSO-$d_6$) 3.45–4.00(a.c., 11H, (δ=3.91, s)), 6.31(d, J=6.4Hz, 1H), 7.60 (a.c., 2H), 7.88(m, 1H), 8.12–8.18(a.c., 2H, (δ=8.15, d, J=6.4Hz)). | (KBr) 2800–2200 (broad), 1640, 1629, 1625, 1609, 1418, 1219. |
| 23 | $CH_3O-$ | 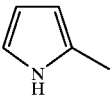 | O | base | B | 142–143 | (300 MHz) ($CDCl_3$) 3.90 (s, 3H), 3.92(a.c., 8H), 6.03 (d, J=5.6Hz, 1H), 6.26(m, 1H), 6.56(m, 1H), 6.94(m, 1H), 8.07(d, J=5.6Hz, 1H), 9.87(m, 1H). | (KBr) 3258, 1586, 1566, 1467, 1433. |
| 24 | $CH_3O-$ | 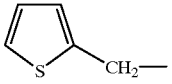 | O | HCl | D | 180–182 (dec) | (300 MHz) (DMSO-$d_6$) 3.86 (a.c., 4H), 3.94(m, 4H), 3.97 (s, 3H), 6.13(m, 1H), 6.41 (d, J=6.7Hz, 1H), 6.56(m, 1H), 6.90(m, 1H), 8.15(d, J=6.7Hz, 1H), 11.52(m, 1H). | (KBr) 3162, 2800–2200 (broad), 1630, 1605, 1487, 1428. |
| 25 | $CH_3O-$ |  | O | base | B | 69–71 | (300 MHz) ($CDCl_3$) 3.57 (m, 2H), 3.72(m, 4H), 3.80 (m, 2H), 3.88(s, 3H), 3.97(s, 2H), 6.02(d, J=5.7Hz, 1H), 6.95(m, 2H), 7.21(m, 1H), 8.05(d, J=5.7Hz, 1H). | (KBr) 1634, 1561, 1440, 1337, 1236. |

TABLE 1-continued

| Example | R₁ | R₂ | X | Base or Salt | Procedure | m.p. (° C.) | $^1$H RMN (MHz) (Solvent) δ | IR, cm$^{-1}$ |
|---|---|---|---|---|---|---|---|---|
| 26 | CH₃O— | 2-thienyl-CH₂— | O | HCl | D | 172–175 | (300 MHz) (DMSO-d₆) 3.63 (m, 2H), 3.70(m, 2H), 3.83 (m, 4H), 3.96(s, 3H), 4.03 (s, 2H), 6.38(d, J=6.6Hz, 1H), 6.96(m, 2H), 7.39(dd, J=4.8Hz, J'=1.7Hz, 1H), 8.15(d, J=6.6Hz, 1H). | (KBr) 2800–2200 (broad), 1667, 1636, 1606, 1411, 1216, 1208. |
| 27 | CH₃O— | 2-methyl-3-thienyl (CH₃ at 3-position) | O | base | B | 87–89 | (300 MHz) (CDCl₃) 2.29 (s, 3H), 3.68(m, 4H), 3.86 (m, 4H), 3.88(s, 3H), 6.03(d, J=5.6Hz, 1H), 6.86(d, J=5.0Hz, 1H), 7.30(d, J=5.0Hz, 1H) 8.06(d, J=5.7Hz, 1H). | (KBr) 1634, 1586, 1567, 1468, 1453, 1260. |
| 28 | CH₃O— | 3-methyl-2-thienyl | O | HCl | D | 144–146 | (300 MHz) (DMSO-d₆) 3.62 (m, 4H), 3.89(m, 4H), 3.94 (s, 3H), 6.37(d, J=6.6Hz, 1H), 6.95(d, J=4.9Hz, 1H), 7.60(d, J=4.9Hz, 1H), 8.14(d, J=6.6Hz, 1H). | (KBr) 2800–2200 (broad), 1617, 1604, 1486, 1427, 1413, 1258. |
| 29 | CH₃O— | 2-methyl-3-chloro-thienyl | O | base | B | 86–88 | (300 MHz) (CDCl₃) 3.55– 3.85(a.c., 4H), 3.89(s, 3H), 3.91(m, 4H), 6.04(d, J=5.7 Hz, 1H), 6.94(d, J=5.1Hz, 1H), 7.40(d, J=5.1Hz, 1H), 8.07(d, J=5.7Hz, 1H). | (KBr) 1622, 1587, 1561, 1509. |
| 30 | CH₃O— | 2-methyl-3-chloro-thienyl | O | HCl | D | 144–147 | (300 MHz) (DMSO-d₆) 3.50– 3.70(a.c., 4H), 3.87(m, 4H), 3.91(s, 3H), 6.31(d, J=6.2 Hz, 1H), 7.14(d, J=5.4Hz, 1H), 7.85(d, J=5.4Hz, 1H), 8.14(d, J=6.2Hz, 1H). | (KBr) 2800–2200 (broad), 1636, 1608, 1481, 1443, 1407. |
| 31 | CH₃O— | 3-methyl-1H-indol-2-yl | O | base | B | 229–231 | (300 MHz) (CDCl₃) 3.80 (m, 4H), 3.84–3.93(a.c., 7H, (δ=3.88, s)), 6.03(d, J= 5.7Hz, 1H), 7.22(m, 2H), 7.38(m, 1H), 7.46(d, J=2.8 Hz, 1H), 7.73(m, 1H), 8.07 (d, J=5.7Hz, 1H), 8.96 (broad singlet, 1H). | (KBr) 3181, 1610, 1590, 1559, 1467, 1339, 998. |
| 32 | CH₃O— | benzo[b]thiophen-3-yl-CH₂— | O | base | B | 135–137 | (300 MHz) (CDCl₃) 3.53 (m, 2H), 3.66(m, 2H), 3.78 (a.c., 4H), 3.86(s, 3H), 3.98 (s, 2H), 6.01(d, J=5.6Hz, 1H), 7.26(s, 1H), 7.40(m, 2H), 7.85(m, 2H), 8.03(d, J=5.6Hz, 1H). | (KBr) 1619, 1590, 1561, 1553, 1454, 990. |
| 33 | CH₃O— | 5-chloro-2-methyl-thienyl | O | base | B | 99–100 | (300 MHz) (CDCl₃) 3.81 (m, 4H), 3.89(m, 4H), 3.90 (s, 3H), 6.04(d, J=5.7Hz, 1H), 6.89(d, J=4.0Hz, 1H), 7.13(d, J=4.0Hz, 1H), 8.07(d, J=5.7Hz, 1H). | (KBr) 1610, 1594, 1584, 1561, 1442 1258. |

TABLE 1-continued

| Example | R₁ | R₂ | X | Base or Salt | Procedure | m.p. (° C.) | ¹H RMN (MHz) (Solvent) δ | IR, cm⁻¹ |
|---|---|---|---|---|---|---|---|---|
| 34 | CH₃O— | 2-chloro-5-methylthiophene | O | HCl | D | 159–162 | (300 MHz) (DMSO-d₆) 3.80 (m, 4H), 3.91(m, 4H), 3.94(s, 3H), 6.35(d, J=6.3Hz, 1H), 7.18(d, J=4.0Hz, 1H), 7.40(d, J=4.0Hz, 1H) 8.15(d, J=6.3Hz, 1H). | (KBr) 2800–2200 (broad), 1639, 1613, 1592, 1436. |
| 35 | CH₃O— | 4-methoxyphenyl | O | base | B | 127–129 | (300 MHz) (CDCl₃) 3.58–3.96(a.c., 14H, (δ=3.84, s, y δ=3.87, s)), 6.02(d, J=5.7Hz, 1H), 6.92(m, J= 8.8Hz, 2H), 7.41(m, J=8.8 Hz, 2H), 8.05(d, J=5.7Hz, 1H). | (KBr) 1624, 1587, 1562, 1433, 1252. |
| 36 | CH₃O— | 4-methoxyphenyl | O | HCl | D | 162–164 | (300 MHz) (CDCl₃) 3.76–3.88(a.c., 7H, (δ=3.85, s)), 3.93–4.36(a.c., 7H, (δ=4.07, s)), 6.29(d, J=6.8Hz, 1H), 6.93(d, J=8.6Hz, 2H), 7.40(d, J=8.6Hz, 2H), 8.10(d, J= 6.8Hz, 1H). | (KBr) 2800–2200 (broad), 1631, 1615, 1484, 1428, 1413, 1260, 1244. |
| 37 | CH₃O— | 4-fluorophenyl | O | base | B | 123–126 | (300 MHz) (CDCl₃) 3.37–4.03(a.c., 11H, (δ=3.89, s)), 6.04(d, J=5.7Hz, 1H), 7.12 (m, J=8.8Hz, 2H), 7.46(m, J=8.8Hz, J'=5.4Hz, 2H), 8.06(d, J=5.7Hz, 1H). | (KBr) 1631, 1584, 1565, 1428, 1340, 1249. |
| 38 | CH₃O— | 4-fluorophenyl | O | HCl | D | 152–156 | (300 MHz) (CDCl₃) 3.80 (m, 4H), 3.98–4.28(a.c., 7H, (δ=4.07, s)), 6.31(d, J= 6.8Hz, 1H), 7.13(t, J=8.6Hz, 2H), 7.44(dd, J=8.6Hz, J'=5.3Hz, 2H), 8.11(d, J=6.8Hz, 1H). | (KBr) 2800–2200 (broad), 1630 (banda intensa), 1485, 1439, 1415, 1355, 1266, 1005. |
| 39 | CH₃O— | 4-chlorophenyl | O | base | B | 143–144 | (300 MHz) (CDCl₃) 3.50 (m, 2H), 3.66–4.01(a.c., 9H, (δ=3.89, s)), 6.04(d, J= 5.6Hz, 1H), 7.40(system AB, J=8.7Hz, 4H), 8.06(d, J=5.6Hz, 1H). | (KBr) 1630, 1580, 1558, 1470, 1439, 1262. |
| 40 | CH₃O— | 4-chlorophenyl | O | HCl | D | 166–168 | (300 MHz) (CDCl₃) 3.80 (m, 4H), 3.97–4.38(a.c., 7H, (δ=4.09, s)), 6.32(d, J= 6.9Hz, 1H), 7.37 and 7.43 (system AB, J=8.6Hz, 4H), 8.11(d, J=6.9Hz, 1H). | (KBr) 2800–2200 (broad), 1631, 1609, 1492, 1431, 1420, 1359, 1262. |
| 41 | CH₃O— | 3-methoxyphenyl | O | base | B | 78–81 | (300 MHz) (CDCl₃) 3.50 (m, 2H), 3.66–4.02(a.c., 12H, (δ=3.83, s y δ=3.88, s)), 6.03(d, J=5.6Hz, 1H), 6.99(a.c., 3H), 7.33(t, J=8.0 Hz, 1H), 8.06(d, J=5.6Hz, 1H). | (KBr) 1630, 1584, 1562, 1430, 1338, 1236. |

TABLE 1-continued

| Example | R₁ | R₂ | X | Base or Salt | Procedure | m.p. (° C.) | $^1$H RMN (MHz) (Solvent) δ | IR, cm$^{-1}$ |
|---|---|---|---|---|---|---|---|---|
| 42 | CH₃O— | 3-methoxyphenyl | O | HCl | D | 158–161 | (300 MHz) (CDCl₃) 3.61–4.38(a.c., 14H, (δ=3.83, s and δ=4.08, s)), 6.30(d, J=6.9Hz, 1H), 6.96(a.c., 3H), 7.34(t, J=8.1Hz, 1H), 8.10(d, J=6.9Hz, 1H). | (KBr) 2800–2200 (broad), 1636, 1605, 1490, 1418, 1270. |
| 43 | CH₃O— | 3-fluorophenyl | O | base | B | 106–107 | (300 MHz) (CDCl₃) 3.49 (m, 2H), 3.66–4.02(a.c., 9H, (δ=3.89, s)), 6.04(d, J=5.6Hz, 1H), 7.19(a.c., 3H), 7.41(m, 1H), 8.06(d, J=5.6Hz, 1H). | (KBr) 1639, 1593, 1582, 1459, 1439, 1342. |
| 44 | CH₃O— | 3-fluorophenyl | O | HCl | D | 153–156 | (300 MHz) (CDCl₃) 3.56–4.43(a.c., 11H, (δ=4.09, s)), 6.32(d, J=6.9Hz, 1H), 7.18(a.c., 3H), 7.43(m, 1H), 8.11(d, J=6.9Hz, 1H). | (KBr) 2800–2200 (broad), 1639, 1610, 1489, 1415, 1288, 1266. |
| 45 | CH₃O— | 3-chlorophenyl | O | base | B | 94–96 | (300 MHz) (CDCl₃) 3.49 (m, 2H), 3.70–4.00(a.c., 9H, (δ=3.89, s)), 6.04(d, J=5.7Hz, 1H), 7.29–7.45 (a.c., 4H), 8.07(d, J=5.7 Hz, 1H). | (KBr) 1645, 1593, 1561, 1433, 1256. |
| 46 | CH₃O— | 3-chlorophenyl | O | HCl | D | 166–170 | (300 MHz) (CDCl₃) 3.60–3.97(a.c., 4H), 3.98–4.37 (a.c., 7H, (δ=4.08, s)), 6.31 (d, J=7.0Hz, 1H), 7.29(m, 1H), 7.42(a.c., 3H), 8.11(d, J=7.0Hz, 1H). | (KBr) 2800–2200 (broad), 1632, 1611, 1597, 1488, 1414, 1286. |
| 47 | CH₃O— | 2-methoxyphenyl | O | base | B | 113–115 | (300 MHz) (CDCl₃) 3.33 (m, 2H), 3.72–3.99(a.c., 12H, (δ=3.84, s y δ=3.88, s)), 6.02(d, J=5.6Hz, 1H), 6.93 (d, J=8.6Hz, 1H), 7.02(m, 1H), 7.28(m, 1H), 7.38(m, 1H), 8.05(d, J=5.6Hz, 1H). | (KBr) 1619, 1584, 1562, 1241. |
| 48 | CH₃O— | 2-methoxyphenyl | O | HCl | D | 163–164 | (300 MHz) (CDCl₃) 3.51 (m, 2H), 3.75–4.33(a.c., 12H, (δ=3.85, s and δ=4.09, s)), 6.28(d, J=7.0Hz, 1H), 6.95 (d, J=8.3Hz, 1H), 7.02(m, 1H), 7.25(m, 1H), 7.40(m, 1H), 8.10(d, J=8.3Hz, 1H). | (KBr) 2800–2200 (broad), 1644, 1628, 1611, 1490, 1261. |
| 49 | CH₃O— | 2-fluorophenyl | O | base | B | 102–103 | (300 MHz) (CDCl₃) 3.40 (broad, 2H), 3.77–3.98(a.c., 9H, (δ=3.89, s)), 6.03(d, J=5.6Hz, 1H), 7.12(m, 1H), 7.23(m, 1H), 7.42(m, 2H), 8.06(d, J=5.6Hz, 1H). | (KBr) 1641, 1595, 1561, 1466. |

TABLE 1-continued

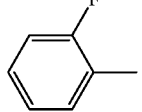

| Example | R₁ | R₂ | X | Base or Salt | Procedure | m.p. (° C.) | ¹H RMN (MHz) (Solvent) δ | IR, cm⁻¹ |
|---|---|---|---|---|---|---|---|---|
| 50 | CH₃O— | 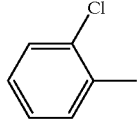 | O | HCl | D | 148–152 | (300 MHz) (CDCl₃) 3.58 (broad, 2H), 3.82–4.39(a.c., 9H, (δ=4.08, s)), 6.31(d, J=6.9Hz, 1H), 7.13(m, 1H), 7.25(m, 1H), 7.44(m, 2H), 8.11(d, J=6.9Hz, 1H). | (KBr) 2800–2200 (broad), 1643, 1612, 1490, 1430, 1418, 1287, 1260. |
| 51 | CH₃O— | 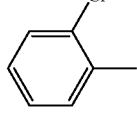 | O | base | B | 112–115 | (300 MHz) (CDCl₃) 3.32 (m, 2H), 3.71–4.00(a.c., 9H, (δ=3.88, s)), 6.03(d, J=5.6Hz, 1H), 7.30–7.46 (a.c., 4H), 8.06(d, J=5.6Hz, 1H). | (KBr) 1640, 1593, 1561. |
| 52 | CH₃O— | 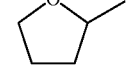 | O | HCl | D | 152–154 | (300 MHz) (CDCl₃) 3.49 (m, 2H), 3.73–4.40(a.c., 9H, (δ=4.08, s)), 6.30(d, J=6.7Hz, 1H), 7.25–7.48 (a.c., 4H), 8.10(d, J=6.7Hz, 1H). | (KBr) 2800–2200 (broad), 1643, 1609, 1492, 1431, 1415, 1288, 1258. |
| 53 | CH₃O— | 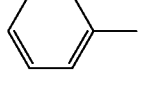 | O | base | B | 90–91 | (300 MHz) (CDCl₃) 1.82–2.13(a.c., 3H), 2.31(m, 1H), 3.58(m, 2H), 3.67–3.82(a.c., 4H), 3.82–3.98(a.c., 7H, (δ=3.87, s)), 4.63(dd, J=7.4Hz, J'=5.3Hz, 1H), 6.00(d, J=5.6Hz, 1H), 8.03(d, J=5.6Hz, 1H) | (KBr) 1653, 1596, 1586, 1564, 1505, 1239, 987. |
| 54 | CH₃O— | 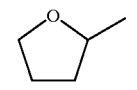 | S | base | C | 125–129 | (300 Mhz) (CDCl₃) 3.68 (m, 2H), 3.82(m, 2H), 3.88(s, 3H), 4.07(m, 2H), 4.48(m, 2H), 6.06(d, J=5.7Hz, 1H), 7.29–7.41(a.c., 5H), 8.08(d, J=5.7Hz, 1H). | (KBr) 1589, 1561, 1470, 1233. |
| 55 | CH₃O— | 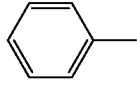 | O | HCl | D | 149–151 | (300 MHz) (CDCl₃) 1.84–2.14(a.c., 2H), 2.30(m, 1H), 3.41–4.53(a.c., 13H, (δ=4.06, s)), 4.57(t, J=6.3Hz, 1H), 6.29(d, J=6.9Hz, 1H), 8.12(d, J=6.9Hz, 1H). | (KBr) 2800–2200 (broad), 1644, 1609, 1491, 1241, 1217. |
| 56 | CH₃O— | 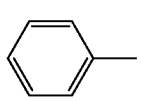 | S | HCl | D | 151–154 | (300 MHz) (CDCl₃) 3.87 (broad, 2H), 4.09(s, 3H), 4.22 (broad, 4H), 4.53(broad, 2H), 6.33(d, J=6.2Hz, 1H), 7.27–7.44(a.c., 5H), 8.12(d, J=6.2Hz, 1H). | (KBr) 2800–2200 (broad) 1637, 1604, 1494, 1212. |
| 57 | CH₃O— | 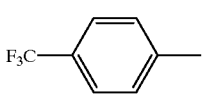 | O | HCl | D | 136–138 | (300 Mhz) (CDCl₃) 3.61–4.37(a.c., 11H, (δ=4.08, s)), 6.30(d, J=7.2Hz, 1H), 7.43(m, 5H), 8.10(d, J=7.2Hz, 1H). | (KBr) 2800–2200 (broad), 1643, 1637, 1629, 1611, 1488, 1265. |
| 58 | CH₃O— | F₃C— | O | base | B | 123–126 | (300 MHz) (CDCl₃) 3.45 (m, 2H), 3.74–3.99(a.c., 9H, (δ=3.88, s)), 6.04(d, J=5.6Hz, 1H), 7.56 and 7.71 (system AB, J=8.0Hz, 4H), 8.06(d, J=5.6Hz, 1H). | (KBr) 1645, 1593, 1561, 1433, 1256. |

TABLE 1-continued

| Example | R₁ | R₂ | X | Base or Salt | Procedure | m.p. (° C.) | ¹H RMN (MHz) (Solvent) δ | IR, cm⁻¹ |
|---------|-----|-----|---|--------------|-----------|-------------|--------------------------|----------|
| 59 | CH₃O— | 4-(F₃C)C₆H₄— | O | HCl | D | 140–143 | (300 MHz) (CDCl₃) 3.57–4.29(a.c., 11H, (δ=4.08, s)), 7.31(d, J=6.7Hz, 1H), 7.55 and 7.73(system AB, J=8.2Hz, 4H), 8.11(d, J=6.7Hz, 1H). | (KBr) 2800–2200 (broad), 1640, 1611, 1491, 1327, 1264. |
| 60 | CH₃O— | 3-(F₃C)C₆H₄— | O | base | B | oil | (300 MHz) (CDCl₃) 3.49 (m, 2H), 3.73–4.00(a.c., 9H, (δ=3.88, s)), 6.04(d, J=5.6Hz, 1H), 7.53–7.78(a.c., 4H), 8.06(d, J=5.6Hz, 1H). | (film) 1643, 1587, 1567, 1332. |
| 61 | CH₃O— | 3-(F₃C)C₆H₄— | O | HCl | D | 177–179 | (300 MHz) (CDCl₃) 3.55–4.40(a.c., 11H, (δ=4.08, s)), 6.32(d, J=7.1Hz, 1H), 7.60(m, 2H), 7.72(m, 2H), 8.11(d, J=7.1Hz, 1H). | (KBr) 2800–2200 (broad), 1637, 1611, 1490, 1333, 1322, 1264. |
| 62 | CH₃O— | 2-(CF₃)C₆H₄— | O | base | B | 93–97 | (300 MHz) (CDCl₃) 3.24 (m, 2H), 3.75(m, 2H), 3.82–3.96(a.c., 7H, (δ=3.87, s)), 6.03(d, J=5.6Hz, 1H), 7.36 (d, J=7.3Hz, 1H), 7.54(t, J=7.6Hz, 1H), 7.62(t, J=7.6Hz, 1H), 7.73(d, J=7.3Hz, 1H), 8.05(d, J=5.6Hz, 1H). | (KBr) 1641, 1587, 1569, 1436, 1341, 1314, 1251 |
| 63 | CH₃O— | 2-(CF₃)C₆H₄— | O | HCl | D | 155–158 | (300 MHz) (CDCl₃) 3.42 (broad singlet, 2H), 3.70–4.43(a.c., 9H, (δ=4.07, s)), 6.30(d, J=7.1Hz, 1H), 7.33 (d, J=7.2Hz, 1H), 7.60(m, 2H), 7.74(d, J=7.2Hz, 1H), 8.08(d, J=7.1Hz, 1H). | (KBr) 2800–2200 (banda ancha), 1645, 1604, 1486, 1317, 1126. |
| 64 | CH₃O— | 3-pyridyl | O | base | B | 102–105 | (300 MHz) (CDCl₃) 3.51 (m, 2H), 3.69–4.00(a.c., 9H, (=3.88, s)), 6.04(d, J=5.6Hz, 1H), 7.39(dd, J=7.7Hz, J'=5.0Hz, 1H), 7.79(d, J=7.7Hz, 1H), 8.06(d, J=5.6Hz, 1H), 8.70(m, 2H). | (KBr) 1623, 1589, 1566, 1439. |
| 65 | CH₃O— | 3-pyridyl | O | 2 HCl | D | 148–151 | (300 MHz) (DMSO-d₆) 3.66–4.42(a.c., 11H, (δ=3.92, s)), 6.32(d, J=6.3Hz, 1H), 7.78 (dd, J=7.9Hz, J'=5.4Hz, 1H), 8.14(d, J=6.3Hz, 1H), 8.22(d, J=7.9Hz, 1H), 8.81(d, J=5.4 Hz, 1H), 8.85(s, 1H). | (KBr) 2800–2200 (broad), 1641, 1609, 1493, 1442, 1268 |
| 66 | CH₃O— | 4-pyridyl | O | base | B | 149–152 | (300 MHz) (CDCl₃) 3.43 (m, 2H), 3.75–3.98(a.c., 9H, (δ=3.88, s)), 6.05(d, J=5.7Hz, 1H), 7.32(m, 2H), 8.06(d, J=5.7Hz, 1H), 8.73 (m, 2H). | (KBr) 1638, 1589, 1561, 1340. |
| 67 | CH₃O— | 4-pyridyl | O | 2 HCl | D | 157–161 | (300 MHz) (DMSO-d₆) 3.42 (m, 2H), 3.73–4.05(a.c., 9H, (δ=3.94, s)), 6.37(d, J=6.5Hz, 1H), 7.98(d, J=5.5Hz, 2H), 8.14(d, J=6.5Hz, 1H), 8.96(d, J=5.5Hz, 1H). | (KBr) 2800–2200 (broad), 1634, 1610, 1488, 1415, 1356, 1287, 1265. |

TABLE 1-continued

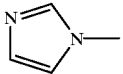

| Example | R₁ | R₂ | X | Base or Salt | Procedure | m.p. (° C.) | ¹H RMN (MHz) (Solvent) δ | IR, cm⁻¹ |
|---|---|---|---|---|---|---|---|---|
| 68 | $CH_3O-$ | 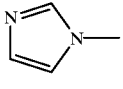 | O | base | B | 127–131 | (300 MHz) (CDCl₃) 3.68 (m, 4H), 3.89(s, 3H), 3.92(m, 4H), 6.06(d, J=5.7Hz, 1H), 7.12(s, 1H), 7.24(s, 1H), 7.91 (s, 1H), 8.07(d, J=5.7Hz, 1H). | (KBr) 1691, 1599, 1556, 1430, 1418, 1241, 988 |
| 69 | $CH_3O-$ | 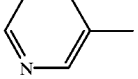 | O | HCl | D | 160–163 | (300 MHz) (DMSO-d₆) 3.68 (m, 4H), 3.95(s, 3H), 3.98(m, 4H), 6.35(d, J=6.0Hz, 1H), 7.82(s, 1H), 8.05(s, 1H), 8.17 (d, J=6.0Hz, 1H), 9.54(s, 1H). | (KBr) 2800–2200 (broad), 1733, 1639, 1612, 1490, 1416 |
| 70 | $CF_3-$ | 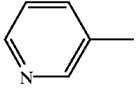 | O | base | B | 125–126 | (300 MHz) (CDCl₃) 3.41– 4.15(a.c., 8H), 6.84(d, J=4.8 Hz, 1H), 7.40(ddd, J=7.9Hz, J'=4.8Hz, J''=0.9Hz, 1H), 7.80(ddd, J=7.9Hz, J'=2.1 Hz, J''=1.8Hz, 1H), 8.53(d, J=4.8Hz, 1H), 8.71(m, 2H). | (KBr) 1631, 1593, 1502, 1434, 1331, 1257, 1158. |
| 71 | $CF_3-$ | 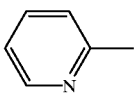 | O | HCl | D | 149–154 | (300 MHz) (DMSO-d₆, TFA) 3.46(m, 2H), 3.67–4.03(a.c., 6H), 7.03(d, J=4.8Hz, 1H), 8.05(dd, J=8.0Hz, J'=5.6Hz, 1H), 8.56(d, J=8.0Hz, 1H), 8.68(d, J=4.8Hz, 1H), 8.95 (d, J=5.6Hz, 1H), 9.04(s, 1H). | (KBr) 2800–2200 (broad), 1634, 1595, 1524, 1435, 1338, 1273, 1186, 981. |
| 72 | $CH_3O-$ | 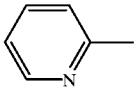 | O | base | B | 108–111 | (300 MHz) (CDCl₃) 3.69 (m, 2H), 3.81–4.02(a.c., 9H, (δ=3.88, s)), 6.02(d, J=5.7 Hz, 1H), 7.37(m, 1H), 7.70(d, J=8.0Hz, 1H), 7.82(dt, J=8.0 Hz, J'=1.7 Hz, 1H), 8.06(d, J=5.7Hz, 1H), 8.61(d, J=5.1 Hz, 1H). | (KBr) 1623, 1595, 1585, 1565, 1473, 1263. |
| 73 | $CH_3O-$ | 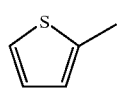 | O | 2 HCl | D | 157–161 | (300 MHz) (DMSO-d₆, TFA) 3.67(broad), 3.79–4.07(a.c., 9H, (δ=3.99, s)), 6.48(d, J=6.5Hz, 1H), 7.63(m, 1H), 7.78(m, 1H), 8.09(m, 1H), 8.19(d, J=6.5Hz, 1H), 8.68 (d, J=4.6Hz, 1H). | (KBr) 2800–2200 (broad), 1650, 1606, 1495, 1444, 1265 |
| 74 | $C_2H_5O-$ | 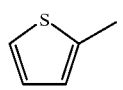 | O | base | B | 97–99 | (300 MHz) (CDCl₃) 1.37 (t, J=7.1Hz, 3H), 3.77–3.93 (a.c., 8H), 4.33(q, J=7.1Hz, 2H), 6.01(d, J=5.6Hz, 1H), 7.07(m, 1H), 7.33(d, J=3.4Hz, 1H), 7.47(d, J=4.9Hz, 1H), 8.06(d, J=5.6Hz, 1H). | (KBr) 1605, 1583, 1560, 1449, 1438, 1258, 1237. |
| 75 | $C_2H_5O-$ | | O | HCl | D | 138–139 | (300 MHz) (CDCl₃) 1.45 (t, J=7.1Hz, 3H), 3.80–4.40 (a.c., (H), 4.50(q, J=7.1Hz, 2H), 6.27(d, J=6.9Hz, 1H), 7.08(dd, J=4.9Hz, J'=3.8Hz, 1H), 7.33(d, J=3.8Hz, 1H), 7.50(d, J=4.9Hz, 1H), 8.10 (d, J=6.9Hz, 1H). | (KBr) 2800–2200 (broad), 1609, 1434, 1257, 994 |

TABLE 1-continued

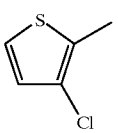

| Example | R₁ | R₂ | X | Base or Salt | Procedure | m.p. (° C.) | ¹H RMN (MHz) (Solvent) δ | IR, cm⁻¹ |
|---|---|---|---|---|---|---|---|---|
| 76 | $C_2H_5O-$ | 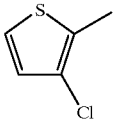 | O | base | B | 91–94 | (300 MHz) (CDCl₃) 1.36 (t, J=7.1Hz, 3H), 3.45–3.97 (a.c., 8H), 4.32(q, J=7.1Hz, 2H), 6.01(d, J=5.6Hz, 1H), 6.93(d, J=5.2Hz, 1H), 7.40 (d, J=5.2Hz, 1H), 8.06(d, J=5.6Hz, 1H). | (KBr) 1625, 1558, 1436, 1255 |
| 77 | $C_2H_5O-$ | 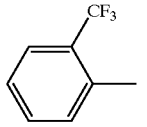 | O | HCl | D | 167–169 | (300 MHz) (CDCl₃) 1.46 (t, J=7.0Hz, 3H), 3.81(broad, 4H), 3.93–4.42(a.c., 4H), 4.51 (q, J=7.0Hz, 2H), 6.28(d, J= 6.9Hz, 1H), 6.95(d, J=5.3Hz, 1H), 7.44(d, J=5.3Hz, 1H), 8.10(d, J=6.9Hz, 1H). | (KBr) 2800–2200 (broad) 1639, 1617, 1604, 1460, 1440, 1292, 1260, 1203. |
| 78 | $C_2H_5O-$ | 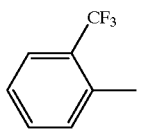 | O | base | B | 99–101 | (300 MHz) (CDCl₃) 1.36 (t, J=7.1Hz, 3H), 3.23(m, 2H), 3.73(m, 2H), 3.88(a.c., 4H), 4.31(q, J=7.1Hz, 2H), 6.00(d, J=5.6Hz, 1H), 7.36 (d, J=7.2Hz, 1H), 7.54(m, 1H), 7.62(m, 1H), 7.73(m, 1H), 8.05(d, J=5.6Hz, 1H). | (KBr) 1624, 1582, 1437, 1258 |
| 79 | $C_2H_5O-$ | 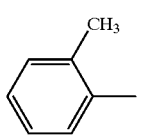 | O | HCl | D | 146–148 | (300 MHz) (CDCl₃) 1.45 (t, J=7.1Hz, 3H), 3.42(broad, 2H), 3.68–4.41(a.c., 6H), 4.50(m, 2H), 6.27(d, J=6.7 Hz, 1H), 7.33(d, J=7.1Hz, 1H), 7.61(m, 2H), 7.74(d, J= 7.9Hz, 1H), 8.07(d, J=6.7Hz, 1H). | (KBr) 2800–2200 (broad), 1640, 1602, 1437, 1320, 1259 |
| 80 | $CH_3O-$ | 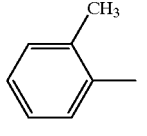 | O | base | B | 70–73 | (300 MHz) (CDCl₃) 2.33 (s, 3H), 3.30(broad, 2H), 3.74 (broad, 2H), 3.83–3.98(a.c., 7H, (δ=3.87, s)), 6.03(d, J=5.5Hz, 1H), 7.15–7.34(m, 4H), 8.05(d, J=5.5Hz, 1H). | (KBr) 1621, 1598, 1559, 1430, 1263 |
| 81 | $CH_3O-$ | 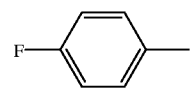 | O | HCl | D | 151–153 | (300 MHz) (CDCl₃) 2.30 (s, 3H), 3.48(broad, 2H), 3.90–4.35(a.c., 9H, (=4.08, s)), 6.29(d, J=6.0Hz, 1H), 7.13–7.32(a.c., 4H), 8.10 (d, J=6.0Hz, 1H). | (KBr) 2800–2200 (broad), 1643, 1630, 1610, 1491, 1415, 1263 |
| 82 | $(CH_3)_2CHO$ | 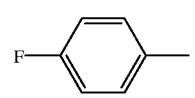 | O | base | B | 112–115 | (300 MHz) (CDCl₃) 1.31 (d, J=6.0Hz, 6H), 3.40–4.00 (a.c., 8H), 5.24(h, J=6.0Hz, 1H), 5.96(d, J=5.7Hz, 1H), 7.13(t, J=7.8Hz, 2H), 7.46 (m, J=8.8Hz, J'=5.4Hz, 2H), 8.03(d, J=5.7Hz, 1H). | (KBr) 1632, 1583, 1557, 1450, 1236 |
| 83 | $(CH_3)_2CHO$ | 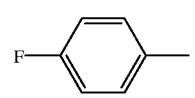 | O | HCl | D | 163–166 | (300 MHz) (CDCl₃) 1.41 (d, J=6.0Hz, 6H), 3.65–4.40 (a.c., 8H), 5.39(m, 1H), 6.22 (d, J=6.9Hz, 1H), 7.13(m, 2H), 7.43(m, 2H), 8.07(d, J=6.9Hz, 1H). | (KBr) 2800–2200 (broad) 1636, 1608, 1458, 1432, 1259 |

TABLE 1-continued

| Example | R₁ | R₂ | X | Base or Salt | Procedure | m.p. (° C.) | ¹H RMN (MHz) (Solvent) δ | IR, cm⁻¹ |
|---|---|---|---|---|---|---|---|---|
| 84 | $(CH_3)_2CHO$ | 2-CF₃-phenyl | O | base | B | — | (300 MHz) (CDCl₃) 1.29 (d, J=6.0Hz, 6H), 3.24(m, 2H), 3.72(m, 2H), 3.89(m, 4H), 5.24(h, J=6.0Hz, 1H), 5.97(d, J=5.7Hz, 1H), 7.36 (d, J=7.2Hz, 1H), 7.58(m, 2H), 7.73(d, J=7.8Hz, 1H), 8.04(d, J=5.7Hz, 1H). | (KBr) 1651, 1581, 1563, 1317 |
| 85 | $(CH_3)_2CHO$ | 2-CF₃-phenyl | O | HCl | D | 159–161 | (300 MHz) (CDCl₃) 1.42 (d, J=5.6Hz, 6H), 3.43(broad, 2H), 3.67–4.44(a.c., 6H), 5.40(m, 1H), 6.22(d, J=6.8 Hz, 1H), 7.33(d, J=6.9Hz, 1H), 7.61(m, 2H), 7.75(d, J=7.5Hz, 1H), 8.05(d, J=6.9Hz, 1H). | (KBr) 2800–2200 (broad), 1640, 1604, 1473, 1317, 1122 |
| 86 | $(CH_3)_2CHO$ | 3-Cl-thien-2-yl | O | base | B | 68–70 | (300 MHz) (CDCl₃) 1.33 (d, J=6.1Hz, 6H), 3.40–4.07 (a.c., 8H), 5.26(h, J=6.1Hz, 1H), 5.97(d, J=5.7Hz, 1H), 6.93(d, J=5.3Hz, 1H), 7.39 (d, J=5.3Hz, 1H), 8.05(d, J=5.7Hz, 1H). | (KBr) 1631, 1583, 1557, 1445 |
| 87 | $(CH_3)_2CHO$ | 3-Cl-thien-2-yl | O | HCl | D | 148–150 | (300 MHz) (CDCl₃) 1.42 (d, J=6.1Hz, 6H), 3.66–4.44 (a.c., 8H), 5.39(h, J=6.1Hz, 1H), 6.23(d, j=5.7Hz, 1H), 6.95(d, J=5.3Hz, 1H), 7.44 (d, J=5.3Hz, 1H), 8.08(d, J=5.7Hz, 1H). | (KBr) 2800–2200 (broad) 1644, 1612, 1462, 1446, 1313, 1282, 1250 |
| 88 | $CH_3O—$ | cyclohexyl | O | base | B | 109–111 | (300 MHz) (CDCl₃) 1.28 (m, 3H), 1.46–1.89(a.c., 7H), 2.50(tt, J=11.2Hz, J'=3.3Hz, 1H), 3.56(m, 2H), 3.69(m, 2H), 3.81(m, 4H), 3.89(s, 3H), 6.02(d, J=5.5Hz, 1H), 8.06(d, J=5.5Hz, 1H). | (KBr) 1629, 1591, 1556, 1339, 1239, 992 |
| 89 | $CH_3O—$ | cyclohexyl | O | HCl | D | 121–124 | (300 MHz) (CDCl₃) 1.27 (m, 3H), 1.53(m, 2H), 1.75 (a.c., 5H), 2.47(m, 1H), 3.75 (broad singlet, 4H), 3.92(m, 2H), 4.07(s, 3H), 4.29(m, 2H), 6.30(d, J=7.0Hz, 1H), 8.11(d, J=7.0Hz, 1H). | (KBr) 2800–2200 (broad), 1632, 1604, 1487, 1431, 1212 |
| 90 | $C_2H_5O—$ | 4-F-phenyl | O | base | B | 136–138 | (300 MHz) (CDCl₃) 1.37 (t, J=7.0Hz, 3H), 3.38–4.00 (a.c., 8H), 4.32(q, J=7.0Hz, 2H), 6.01(d, J=5.7Hz, 1H), 7.12(t, J=8.5Hz, 2H), 7.45 (m, 2H), 8.06(d, J=5.7Hz, 1H). | (KBr) 1616, 1590, 1557, 1432 |
| 91 | $C_2H_5O—$ | 4-F-phenyl | O | HCl | D | 155–157 | (300 MHz) (CDCl₃) 1.46 (t, J=7.0Hz, 3H), 3.67–4.38 (a.c., 8H), 4.51(q, J=7.0Hz, 2H), 6.28(d, J=6.8Hz, 1H), 7.14(t, J=8.8Hz, 2H), 7.45 (m, 2H), 8.11(d, J=6.8Hz, 1H). | (KBr) 2800–2200 (broad), 1636, 1606, 1458, 1436, 1258 |

TABLE 1-continued

| Example | R₁ | R₂ | X | Base or Salt | Procedure | m.p. (° C.) | ¹H RMN (MHz) (Solvent) δ | IR, cm⁻¹ |
|---|---|---|---|---|---|---|---|---|
| 92 | $CH_3O-$ | 2-methylthiazole | O | base | B | 106–108 | (300 MHz) (CDCl₃) 3.85–3.99(a.c., 9H, (δ=3.90, s)), 4.50(m, 2H), 6.03(d, J=5.7Hz, 1H), 7.56(d, J=3.2Hz, 1H), 7.91(d, J=3.2Hz, 1H), 8.07 (d, J=5.7Hz, 1H) | (KBr) 1596, 1565, 1496, 1442, 1257, 1004 |
| 93 | $CH_3O-$ | 2-aminotoluene | O | base | B | 145–147 | (300 MHz) (CDCl₃) 3.70 (broad, 4H), 3.83–3.90(a.c., 7H, (δ=3.88, s)), 4.35(s, 2H), 6.03(d, J=5.6Hz, 1H), 6.74 (m, 2H), 7.11(m, 1H), 8.06(d, J=5.6Hz, 1H). | (KBr) 3444, 3323, 1617, 1586, 1566, 1498, 1467, 1260 |
| 94 | $CH_3O-$ | 2-aminotoluene | O | 2 HCl | D | 155–157 | (300 MHz) (DMSO-d₃) 3.61 (broad, 4H), 3.94(s, 7H), 6.37 (d, J=6.5Hz, 1H), 7.10(t, J=7.5Hz, 1H), 7.20(d, J=7.5Hz, 1H), 7.32(d, J=7.5Hz, 1H), 7.38(t, j=7.5Hz, 1H), 8.14(d, J=6.5Hz, 1H). | (KBr) 3700–2200 (broad), 1614, 1493, 1439, 1257. |
| 95 | $CH_3O-$ | 3-fluoro-2-methylthiophene | O | base | B | oil | (300 MHz) (CDCl₃) 3.73 (broad, 4H), 3.86–3.99(a.c., 7H, (δ=3.89, s)), 6.03(d, J=5.7Hz, 1H), 6.78(d, J=5.4 Hz, 1H), 7.37(dd, J=5.4Hz, J'=3.7Hz, 1H), 8.06(d, J=5.7Hz, 1H). | (KBr) 1626, 1586, 1469, 1443 |
| 96 | $CH_3O-$ | 3-fluoro-2-methylthiophene | O | HCl | D | 156–157 | (300 MHz) (CDCl₃) 3.86 (broad singlet, 4H), 4.08(s, 5H), 4.23–4.45(m, 2H), 6.31 (d, J=6.9Hz, 1H), 6.80(d, J=5.5Hz, 1H), 7.41(dd, J=5.5Hz, J'=3.7Hz, 1H), 8.12 (d, J=6.9Hz, 1H). | (KBr) 2800–2200 (broad), 1618, 1482, 1413, 1262, 995 |
| 97 | $CH_3O-$ | 2-methylbenzoic acid | O | — | B | 186–188 | (300 MHz) (CDCl₃) 3.25 (m, 2H), 3.65–3.99(a.c., 9H, (δ=3.86, s)), 6.02(d, J= 5.8Hz, 1H), 7.30(d, J=7.6Hz, 1H), 7.45(t, J=7.6Hz, 1H=, 7.57(t, J=7.6Hz, 1H), 8.06 (m, 2H). | (KBr) 3600–2500 (broad), 1711, 1583, 1444, 1342, 1266 |
| 98 | $CH_3O-$ | 2-methylphenyl acetate | O | base | B | 139–142 | (300 Mhz) (CDCl₃) 2.27 (s, 3H), 3.38(m, 2H), 3.74–3.94(a.c., 9H, (=3.87, s)), 6.03(d, J=5.7Hz, 1H), 7.18 (d, J=8.2Hz, 1H), 7.32(m, 2H), 7.44(m, 1H), 8.05(d, J= 5.7Hz, 1H) | (KBr) 1764, 1637, 1566, 1429, 1338, 1259, 1194 |
| 99 | $CH_3O-$ | 2-methylphenol | O | base | B | 186–188 | (300 MHz) (CDCl₃) 3.80 (m, 4H), 3.86–3.95(a.c., 7H), (δ=3.89)), 6.04(d, J=5.7Hz, 1H), 6.87(t, J=7.5Hz, 1H), 7.03(d, J=8.1Hz, 1H), 7.28(m, 1H), 7.35(m, 1H), 8.06(d, J= 5.7Hz, 1H). | (KBr) 3500–2500 (broad), 1566, 1443, 1335, 1229. |

TABLE 1-continued

| Example | R₁ | R₂ | X | Base or Salt | Procedure | m.p. (° C.) | ¹H RMN (MHz) (Solvent) δ | IR, cm⁻¹ |
|---|---|---|---|---|---|---|---|---|
| 100 | $CH_3O-$ | 2-methylphenyl-C(O)ONa | O | — | D | — | (300 MHz) (DMSO-$d_6$) 3.06 (m, 2H), 3.38–3.72(a.c., 4H), 3.79(s, 3H), 3.92(m, 2H), 6.04(d, J=5.4Hz, 1H), 7.02 (m, 1H), 7.27(m, 2H), 7.79 (m, 1H), 8.06(d, J=5.4Hz, 1H). | (KBR) 1624, 1588, 1563, 1382. |
| 101 | $CH_3O-$ | 2-methylphenyl-OH | O | HCl | D | 158–159 | (300 MHz) (DMSO-$d_6$) 3.34 (m, 2H), 3.62–4.01(a.c., 9H, (δ=3.93)), 6.36(d, J=6.3Hz, 1H), 6.84(t, J=7.2Hz, 1H), 6.91(d, J=8.1Hz, 1H), 7.15 (m, 1H), 7.23(m, 1H), 8.13 (d, J=6.3Hz, 1H). | (KBr) 3500–2500 (broad), 1622, 1493, 1361, 1289, 1211. |
| 102 | $CH_3O-$ | pyridin-2-yl | O | HCl | D | 151–153 | (300 MHz) (CDCl₃) 3.93 (broad s, 4H), 4.00–4.40(a.c., 7H, (δ=4.07, s)), 6.29(d, J=6.8Hz, 1H), 7.40(m, 1H), 7.72(broad d, J=7.2Hz, 1H), 7.84(dt, J=7.6Hz, J'=1.7Hz, 1H), 8.11(d, J=6.8Hz, 1H), 8.59(d, J=5.0Hz, 1H). | (KBr) 3500–2500 (broad), 1616, 1486, 1413, 1311, 1212. |
| 103 | $CH_3O-$ | 2-methylphenyl-O-$CH_3$ | O | $NO_3H$ | D | 137–139 | (300 MHz) (CDCl₃) 3.31–3.64(a.c., 2H), 3.70–4.24(a.c., 12H, (δ=3.85, s) (δ=4.08, s)), 6.30(d, J=6.9Hz, 1H), 6.95 (8.2Hz, 1H), 8.23(d, J=6.9Hz, 1H). | (KBr) 3500–2500 (broad), 1646, 1485, 1281, 1000, 750. |
| 104 | $CH_3O-$ | 3-chloro-2-methylthiophene | O | $NO_3H$ | D | 129–131 | (300 Mhz) (CDCl₃) 3.81 (broad, 4H), 4.02(broad, 4H), 4.08(s, 3H), 6.33(d, J=7.0 Hz, 1H), 6.95(d, J=5.0Hz, 1H), 8.25(d, J=7.0Hz, 1H) | (KBr) 3500–2500 (broad), 1643, 1486, 1411, 1258, 077 |
| 105 | $CH_3CH_2O-$ | pyridin-2-yl | O | base | B | 87–900 | (300 Mhz) (CDCl₃) 1.36 (t, J=7.0Hz, 3H), 3.68(m, 2H), 3.78–3.99(a.c., 6H), 4.33(q, J=7.0Hz, 2H), 6.00 (d, J=5.6Hz, 1H), 7.69(d, J=7.9Hz, 1H), 7.82(dt, J=7.9 Hz, J'=1.5Hz, 1H), 8.05 (d, J=5.6Hz, 1H), 8.60(d, J=4.8Hz, 1H). | (KBr) 1634, 1578, 1557, 1447, 1237, 1000 |

Sleep-inducing Activity in Mice

The sleep-inducing activity of the products of the present invention have been studied, evaluating the their capacity to increase the sleep time induced by barbital, according to a modification of the method described by David Sudgen (*J. Pharmacol. Exp. Ther.*, 1983, 227, 3).

Fifteen minutes after the administration of barbital (150 mg/Kg, i.v.), the mice were treated with the product of the study at an initial dose of 100 mg/Kg (i.p.). For the most active products a dosage efficacy 50 ($DE_{50}$) was determined. The results for some of the products of the invention are shown in Table 2, taking meprobamate as the reference product.

TABLE 2

Capacity to increase the sleep time induced by barbital

| Example | % Activity (sleep) Dosage 100 mg/kg | $DE_{50}$ (mg/kg) |
|---|---|---|
| 2 | 93 | 14.4 |
| 4 | 100 | 8.7 |
| 8 | 97 | 9.7 |
| 9 | 67 | 28.1 |
| 10 | 74 | 11.6 |
| 11 | 89 | 10.5 |

TABLE 2-continued

Capacity to increase the sleep time induced by barbital

| Example | % Activity (sleep) Dosage 100 mg/kg | $DE_{50}$ (mg/kg) |
|---|---|---|
| 13 | 77 | 41.3 |
| 15 | 86 | 8.2 |
| 17 | 56 | 84.2 |
| 18 | 82 | 27.3 |
| 22 | 57 | 75 |
| 24 | 69 | 41.5 |
| 26 | 60 | 74.1 |
| 30 | 75 | 37.2 |
| 32 | 73 | 56.5 |
| 34 | 98 | 7 |
| 55 | 70 | 31 |
| 57 | 100 | 1.6 |
| 59 | 101 | 14 |
| 61 | 102 | 4.5 |
| 63 | 103 | 4 |
| 65 | 100 | 7.7 |
| 67 | 96 | 15 |
| 69 | 97 | 10 |
| 73 | 98 | 9.5 |
| 81 | 99 | 8.3 |
| 83 | 100 | 5.3 |
| 87 | 101 | 10 |
| 89 | 102 | 8 |
| 91 | 81 | 10 |
| 92 | 98 | 8 |
| 94 | 84 | 5.2 |
| 96 | 97 | 3 |
| Meprobamate | 54 | 84.5 |

General Anaesthetic Activity

The general anaesthetic activity was study in mice, injecting the product of the study in the caudal vein. The start and duration time of sleep were recorded. The results for some of the products of the patent are shown in Table 3 and it can be seen that they show a clear anaesthetic activity with respect to the reference compound (Propofol), with the animals recovering later.

TABLE 3

Anaesthetic activity in mice. I.V. administration

| Example | Dosage (mg/kg) | Start (s) | Duration (min) |
|---|---|---|---|
| 2 | 80 | Immediate | 5.3 |
|  | 40 | 12 | 0.6 |
| 4 | 80 | Immediate | 7.4 |
|  | 40 | 15 | 1.3 |
| 15 | 80 | 20 | 1.9 |
|  | 40 | 15 | 1.4 |
| 30 | 80 | 30 | 7.9 |
|  | 40 | 30 | 1.8 |
| 34 | 80 | Immediate | 1.5 |
|  | 40 | No | 0 |
| 57 | 80 | Immediate | 11 |
| 59 | 80 | 20 | 3.4 |
| 61 | 80 | 10 | 1.6 |
| 65 | 80 | 20 | 8.6 |
| 63 | 80 | Immediate | 14.8 |
| 71 | 80 | 60 | 5.6 |
| 73 | 80 | Immediate | 9 |
| 77 | 80 | Immediate | 10 |
| 79 | 80 | Immediate | 19 |
| 81 | 80 | Immediate | 10 |
| 85 | 80 | Immediate | 8.4 |
| 87 | 80 | Immediate | 10 |
| 89 | 80 | Immediate | 4 |
| 91 | 80 | Immediate | 7 |
| 92 | 80 | Immediate | 5 |
| 96 | 80 | Immediate | 6 |
| 101 | 80 | Immediate | 2 |

TABLE 3-continued

Anaesthetic activity in mice. I.V. administration

| Example | Dosage (mg/kg) | Start (s) | Duration (min) |
|---|---|---|---|
| Propofol | 106 | 30 | 6.2 |
|  | 120 | 20 | 3.9 |
|  | 80 | No | 0 |

Sedative Activity

The sedative activity of some of the products on the locomotive activity of mice at different dosages has been studied. The technique described by T. G. Heffieren J. Pharm. Exp. Ther., 1989, 251, 105–112 has been followed. The measurement of the locomotive activity is carried out by dividing the rats into groups of four and determining the movement of the animals in an automated fashion using a video installation and the SMART program (Letica S. A.) for image analysis. The measurement of activity started 5 minutes after the administration of the product via i.p. and continued for twenty minutes. The results (FIG. 1) show the sedative effect of the compounds tested.

Muscular Relaxant Activity

The muscular relaxant activity has been studied in the products of the invention by evaluated their effect on the abdominal body tone of mice, following the method described by S. IRWING (Gordon Res. Conf On Medicinal Chem., 1959, p. 133).

The mice received the products under study at a dosage of 80 mg/kg, via I.p., and at different times after administration (½, 1, 2, 3, 4 and 5 hours) the body tone and the abdominal tone was evaluated looking at the muscular tension compared to the control animals.

The results listed in Table 4 show that many of the products are noticeably active as muscular relaxants. This effect lasts longer than for propofol or zolpidem, which were used as reference products.

TABLE 4

Miorelaxant activity in the Irwing mouse test. [Dosage = 80 mg/kg, i.p.]

| | % muscular relaxation at a time of: | | | | | |
|---|---|---|---|---|---|---|
| Example | ½ H | 1 H | 2 H | 3 H | 4 H | 5 H |
| 4 | 100 | 90 | 10 | 0 | 0 | 0 |
| 34 | 60 | 70 | 80 | 85 | 40 | 40 |
| 57 | 100 | 100 | 100 | 80 | 55 | 0 |
| 63 | 100 | 100 | 90 | 75 | 20 | 0 |
| 71 | 100 | 100 | 100 | 40 | 10 | 0 |
| 73 | 100 | 100 | 100 | 0 | 0 | 0 |
| 75 | 100 | 100 | 100 | 80 | 80 | 60 |
| 77 | 100 | 100 | 100 | 60 | 0 | 0 |
| 79 | 100 | 100 | 100 | 65 | 0 | 0 |
| 83 | 90 | 90 | 90 | 70 | 50 | 0 |
| 92 | 100 | 100 | 100 | 0 | 0 | 0 |
| propofol | 100 | 100 | 70 | 0 | 0 | 0 |

Analgesic Activity

The analgesic activity of the products of the invention have been studied by evaluation of their effect in the test of contortions induced by phenylbenzoquinone in mice, following the method described by Siegmund E., and coworkers (Proc. Soc. Exp. Biol. Med. 1957, 95: 729–731).

The mice received the products of the study, a different dosage levels, and one later they received an injections i.p. of 5 mg/kg of phenylbenzoquinone. The portions of the mice were registered for the following fifteen minutes and compared the contortions of the control group. The $DE_{50}$ (dosage efficacy 50) of the pound of Example 4 is shown. This compound showed a better analgesic activity aspirin, both when administered subcutaneously and orally.

TABLE 5

Analgesic activity. Protection from contortions induced by phenylbenzoquinone in mice.

| Example | DE$_{50}$ (mg/kg, s.c.) | DE$_{50}$ (mg/kg, o.a.) |
|---------|------------------------|------------------------|
| Aspirin | 84 | 120 |
| 4 | 48 | 72 |

Pharmaceutical Formulations
1. For injections (im/iv):
   Compound of Example 4 5 mg
   Sodium chloride c.s.
   HCl 0.1 N or NaOH c.s.
   Water for injection c.s.p. 3 ml
2. Capsules
   Compound of Example 4 0.5 to 4.0 mg
   Colloidal silicon dioxide 0.5 mg
   Magnesium stearate 1.0 mg
   Lactose c.s.p. 100 mg
3. Tablets
   Compound of Example 4 0.5 to 4.0 mg
   Colloidal silicon dioxide 0.5 mg
   Magnesium stearate 1.0 mg
   Sodium croscarmelose 60 mg
   Lactose c.s.p. 100 mg
Formula B (Humid Granulation)
   Compound of Example 4 0.5 to 4.0 mg
   Colloidal silicon dioxide 0.5 mg
   Magnesium stearate 1.0 mg
   Povidone K-30 5.0 mg
   Sodium carboxymethylstarch 5.0 mg
   Microcrystalline cellulose 20 mg
   Lactose c.s.p. 100 mg
What is claimed is:
1. Acyl-piperazinyl-pyrimidines of formula (I)

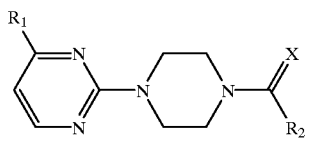

(I)

where
  X is an oxygen or sulfur atom;
  $R_1$ is a $C_{1-4}$ alkoxy or trifluoromethyl radical;
  $R_2$ is a $C_{3-6}$ saturated cycloalkyl; heterocycloalkyl consisting of a ring of 3 to 6 atoms in which the heteroatom is selected from an atom of oxygen, sulfur or nitrogen, optionally N-substituted with $C_{1-6}$ alkyl; phenyl optionally substituted with 1, 2 or 3 identical or different substituents selected from fluorine, chlorine, bromine, amino, acetamido, nitro, methyl, trifluoromethyl and methoxy; arylalkyl consisting of a $C_{1-3}$ alkyl group substituted by a phenyl radical optionally substituted by 1, 2 or 3 identical or different substituents selected from fluorine, chlorine, bromo, amino, acetamido, nitro, methyl, trifluoromethyl and methoxy; heteroaryl consisting of a 5 or 6 heteroatom ring, optionally substituted, or of fused heteroaromatic systems optionally substituted, of 9 or 10 atoms consisting of 1 or 2 heteroatoms selected from oxygen, sulfur and nitrogen, selecting the aforementioned substituents from fluorine, chlorine, bromine, amino, acetamido, nitro, methyl, trifluoromethyl and methoxy; and heteroarylalkyl consisting of an alkyl group of 1 to 3 carbon atoms substituted with a heteroaryl radical consisting of a 5 or 6 member heteroaromatic ring, optionally substituted, or of fused 9 to 10 member heteroaromatic systems, optionally substituted with 1 or 2 heteroatoms selected from oxygen, sulfur and nitrogen, selecting the aforementioned substituents from fluorine, chlorine, bromine, amino, acetamido, nitro, methyl, trifluoromethyl and methoxy, with the proviso that $R_2$ is not 3,4-dimethoxyphenyl; and their physiologically acceptable salts.

2. A compound according to claim 1, in which $R_1$ is methoxy, ethoxy, propoxy, isopropoxy, butoxy, sec-butoxy or tert-butoxy.

3. A compound according to claim 1, in which $R_2$ is cyclopropyl, cyclobutyl, cyclopentyl or cyclohexyl.

4. A compound according to claim 1, in which $R_2$ is 2-azyridinyl, 2-tetrahydrofuryl, 3-tetrahydrofuryl, 2-tetrahydrothienyl, 3-tetrahydrothienyl, 2-azetidinyl, 2-pyrrolidinyl, 3-pyrrolidinyl, 2-piperidinyl, 3-piperidinyl or 4-piperidinyl.

5. A compound according to claim 1, in which $R_2$ is 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-aminophenyl, 3-aminophenyl, 4-aminophenyl, 2-nitrophenyl, 3-nitrophenyl, 4-nitrophenyl, 2-acetamidophenyl, 3-acetamidophenyl, 4-acetamidophenyl, 2-nitrophenyl, 3-nitrophenyl, 4-nitrophenyl, 2-methylphenyl, 3-methylphenyl, 4-methylphenyl, 2-(trifluoromethyl)phenyl, 3-(trifluoromethyl)phenyl, 4-(trifluoromethyl)phenyl, 2-methoxyphenyl, 3-methoxyphenyl, 4-methoxyphenyl, 2,3-difluorophenyl, 3,4-difluorophenyl, 2,4-difluorophenyl, 2,3-dibromophenyl, 3,4-dibromophenyl, 2,4-dibromophenyl, 2,3-dimethylphenyl, 3,4-dimethylphenyl, 2,4-dimethylphenyl, 2,8-dimethoxyphenyl, or 2,4-dimethoxyphenyl.

6. A compound according to claim 1, in which $R_2$ is phenylmethyl, 1-phenylethyl, 2-phenylethyl, or 3-phenylpropyl, optionally substituted at the aromatic ring.

7. A compound according to claim 1, in which $R_2$ is 2-furyl, 3-furyl, 2-thienyl, 3-thienyl, 3-methyl-2-thienyl, 5-methyl-2-thienyl, 3-methoxy-2-thienyl, 3-chloro-2-thienyl, 5-chloro-2-thienyl, 2-pyrrolyl, 3-pyrrolyl, 2-pyridyl, 3-pyridyl, 4-pyridyl, 2-indolyl, 3-indolyl, 2-benzo[b]thienyl, 3-benzyo[b]thienyl, 3-chloro-2-benzo [b]thienyl, pirazolyl, imidazolyl, pyrimidinyl, piridazinyl, pirazinyl, benzimidazolyl, quinolyl, oxazolyl or thiazolyl.

8. A compound according to claim 1, in which $R_2$ is 2-thienylmethyl, 2-benzo[b]thienmethyl or 3-(4-chloropirazolyl)propyl.

9. A compound according to claim 1, selected from the following group:
  2-[4-(2-furylcarbonyl)-1-piperazinyl]-4-methoxypyrimidine,
  2-[4-(2-furylcarbonyl)-1-piperazinyl]-4-methoxypyrimidine chlorohydrate,
  4-methoxy-2-[4-(2-thienylcarbonyl)-1-piperazinyl]pyrimidine, 4-methoxy-2-[4-(2-thienylcarbonyl)-1-piperazinyl]pyrimidine chlorohydrate,
2-(4-acetyl-1-piperazinyl)-4-methoxypyrimidine,
2-{4-[4-(4-chloropyrazolyl)butanoyl]-1-piperazinyl}-4-methoxypyrimidine,
2-{4-[4-(4-chloropyrazolyl)butanoyl]-1-piperazinyl}-4-methoxypyrimidine chlorohydrate,
2-(4-benzoyl-1-piperazinyl)-4-methoxypyrimidine,
2-(4-cyclopropylcarbonyl-1-piperazinyl)-4-methoxypyrimidine,
2-[4-(2-furylcarbonyl)-1-piperazinyl]4-(trifluoromethyl)pyrimidine,
2-[4-(2-thienylcarbonyl)-1-piperazinyl]-4-(trifluoromethyl)pyrimidine,
4-methoxy-2-[4-(3-thienylcarbonyl)-1-piperazinyl]pyrimidine,
4-methoxy-2-[4-(3-thienylcarbonyl)-1-piperazinyl]pyrimidine chlorohydrate,
2-[4-(5-methyl-2-thienylcarbonyl)-1-piperazinyl]-4-methoxypyrimidine,
2-[4-(5-methyl-2-thienylcarbonyl)-1-piperazinyl]-4-methoxypyrimidine chlorohydrate,
4-methoxy-2-[4-(3-methoxy-2-thienylcarbonyl)-1-piperazinyl]pyrimidine,
4-methoxy-2-[4-(3-methoxy-2-thienylcarbonyl)-1-piperazinyl]pyrimidine chlorohydrate,
2-[4-(2-benzo[b]thienylcarbonyl)-1-piperazinyl]-4-methoxypyrimidine,
2-[4-(2-benzo[b]thienylcarbonyl)-1-piperazinyl]-4-methoxypyrimidine chlorohydrate,
2-[4-(2-indolylcarbonyl)-1-piperazinyl]-4-methoxypyrimidine,
2-[4-(3-chloro-2-benzo[b]thienylcarbonyl)-1-piperazinyl]-4-methoxypyrimidine,
2-[4-(3-chloro-2-benzo[b]thienylcarbonyl)-1-piperazinyl]-4-methoxypyrimidine chlorohydrate,
4-methoxy-2-[4-(2-pyrrolylcarbonyl)-1-piperazinyl]pyrimidine,
4-methoxy-2-[4-(2-pyrrolylcarbonyl)-1-piperazinyl]pyrimidine chlorohydrate,
4-methoxy-2-[4-(2-thienylacetyl)-1-piperazinyl]pyrimidine,
4-methoxy-2-[4-(2-thienylacetyl)-1-piperazinyl]pyrimidine chlorohydrate,
2-[4-(3-methyl-2-thienylcarbonyl)-1-piperazinyl]-4-methoxypyrimidine,
2-[4-(3-methyl-2-thienylcarbonyl)-1-piperazinyl]-4-methoxypyrimidine clorohydrate,
2-[4-(3-chloro-2-thienylcarbonyl)-1-piperazinyl]-4-methoxypyrimidine,
2-[4-(3-chloro-2-thienylcarbonyl)-1-piperazinyl]-4-methoxypyrimidine chlorohydrate,
2-[4-(3-indolylcarbonyl)-1-piperazinyl]-4-methoxypyrimidine,
2-[4-(3-benzo[b]thienylacetyl)-1-piperazinyl]-4-methoxypyrimidine,
2-[4-(5-chloro-2-thienylcarbonyl)-1-piperazinyl]-4-methoxypyrimidine,
2-[4-(5-chloro-2-thienylcarbonyl)-1-piperazinyl]-4-methoxypyrimidine chlorohydrate,
4-methoxy-2-[4-(4-chlorobenzoyl)-1-piperazinyl]-4-methoxypyrimidine,
4-methoxy-2-[4-(4-chlorobenzoyl)-1-piperazinyl]-4-methoxypyrimidine chlorohydrate,
2-[4-(4-fluorobenzoyl)-1-piperazinyl]-4-methoxypyrimidine,
2-[4-(4-fluorobenzoyl)-1-piperazinyl]-4-methoxypyrimidine chlorohydrate,
2-[4-(4-chlorobenzoyl)-1-piperazinyl]-4-methoxypyrimidine,
2-[4-(4-chlorobenzoyl)-1-piperazinyl]-4-methoxypyrimidine chlorohydrate,
4-methoxy-2-[4-(3-methoxybenzoyl)-1-piperazinyl]pyrimidine,
4-methoxy-2-[4-(3-methoxybenzoyl)-1-piperazinyl]pyrimidine chlorohydrate,
2-[4-(3-fluorobenzoyl)-1-piperazinyl]-4-methoxypyrimidine,
2-[4-(3-fluorobenzoyl)-1-piperazinyl]-4-methoxypyrimidine chlorohydrate,
2-[4-(3-chlorobenzoyl)-1-piperazinyl]-4-methoxypyrimidine,
2-[4-(3-chlorobenzoyl)-1-piperazinyl]-4-methoxypyrimidine chlorohydrate,
4-methoxy-2-[4-(2-methoxybenzoyl)-1-piperazinyl]pyrimidine,
4-methoxy-2-[4-(2-methoxybenzoyl)-1-piperazinyl]pyrimidine chlorohydrate,
2-[4-(2-(fluorobenzoyl)-1-piperazinyl]-4-methoxypyrimidine,
2-[4-(2-(fluorobenzoyl)-1-piperazinyl]-4-methoxypyrimidine chlorohydrate,
2-[4-(2-(chlorobenzoyl)-1-piperazinyl]-4-methoxypyrimidine,
2-[4-(2-(chlorobenzoyl)-1-piperazinyl]-4-methoxypyrimidine chlorohydrate,
4-methoxy-2-[4-(2-tetrahydrofurylcarbonyl)-1-piperazinyl]pyrimidine,
4-methoxy-2-(4-thiobenzoyl-1-piperazinyl)pyrimidine,
4-methoxy-2-[4-(2-tetrahydrofurylcarbonyl)-1-piperazinyl]pyrimidine chlorohydrate,
4-methoxy-2-(4-thiobenzoyl-1-piperazinyl)pyrimidine chlorohydrate,
2-(4-benzoyl-1-piperazinyl)-4-methoxypyrimidine,
4-methoxy-2-{4-[4-(trifluoromethyl)benzoyl]-1-piperazinyl}pyrimidine,
4-methoxy-2-{4-[4-(trifluoromethyl)benzoyl]-1-piperazinyl}pyrimidine chlorohydrate,
4-methoxy-2-{4-[3-(trifluoromethyl)benzoyl]-1-piperazinyl}pyrimidine,
4-methoxy-2-{4-[3-(trifluoromethyl)benzoyl]-1-piperazinyl}pyrimidine chlorohydrate,
4-methoxy-2-{4-[2-(trifluoromethyl)benzoyl]-1-piperazinyl}pyrimidine,
4-methoxy-2-{4-[2-(trifluoromethyl)benzoyl]-1-piperazinyl}pyrimidine chlorohydrate,
4-methoxy-2-(4-nicotinoyl-1-piperazinyl)pyrimidine,
4-methoxy-2-(4-nicotinoyl-1-piperazinyl)pyrimidine dichlorohydrate,
2-(4-isonicotinoyl-1-piperazinyl)-4-methoxypyrimidine,
2-(4-isonicotinoyl-1-piperazinyl)-4-methoxypyrimidine dichlorohydrate,
2-[4-(1-imidazolylcarbonyl)-1-piperazinyl]-4-methoxypyrimidine,
2-[4-(1-imidazolylcarbonyl)-1-piperazinyl]-4-methoxypyrimidine chlorohydrate,
2-(4-nicotinoyl-1-piperazinyl)-4-(trifluoromethyl)pyrimidine,
2-(4-nicotinoyl-1-piperazinyl)-4-(trifluoromethyl)pyrimidine chlorohydrate,
4-methoxy-2[-4-(2-pyridylcarbonyl)-1-piperazinyl]pyrimidine,
4-methoxy-2[-4-(2-pyridylcarbonyl)-1-piperazinyl]pyrimidine dichlorohyde,
4-ethoxy-2-[4-(2-thienylcarbonyl)-1-piperazinyl]pyrimidine, 4-ethoxy-2-[4-(2-thienylcarbonyl)-1-piperazinyl]
  pyrimidine chlorohydrate,
2-[4-(3-chloro-2-thienylcarbonyl)-1-piperazinyl]-4-
  ethoxypyrimidine,
2-[4-(3-chloro-2-thienylcarbonyl)-1-piperazinyl]-4-
  ethoxypyrimidine chorohydrate,
4-ethoxy-2-{4-[2-(trifluoromethyl)benzoyl]-1-
  piperazinyl}pyrimidine,
4-ethoxy-2-{4-[2-(trifluoromethyl)benzoyl]-1-
  piperazinyl}pyrimidine chlorohydrate,
2-[4-(2-methylbenzoyl)-1-piperazinyl]-4-
  methoxypyrimidine,
2-[4-(2-methylbenzoyl)-1-piperazinyl]-4-
  methoxypyrimidine chlorohydrate,
2-[4-(4-fluorobenzoyl)-1-piperazinyl]-4-
  isopropoxypyrimidine,
2-[4-(4-fluorobenzoyl)-1-piperazinyl]-4-isopropoxy pyrimidine chlorohydrate,
4-isopropoxy-2-{4-[2-(trifluoromethyl)berzoyl]-1-
  piperazinyl]pyrimidine
4-isopropoxy-2-{4-[2-(trifluoromethyl)benzoyl]-1-
  piperazinyl]pyrimidine chlorohydrate,
2-[4-(3-chloro-2-thiencarbonyl)-1-piperazinyl]-4-
  isopropoxypyrimidine,
2-[4-(3-chloro-2-thiencarbonyh)-1-piperazinyl]-4-
  isopropoxypyrimidine chlorohydrate
2-[4-(cyclohexylcarbonyl)-1-piperazinyl]-4-
  methoxypyriridine,
2-[4-(cyclohexylcarbonyl)-1-piperazinyl]-4-
  methoxypyrimidine chorohydrate,
4-ethoxy-2[4-(4-fluorobenzoyl]-1-piperazinyl}pyrimidine,
4-ethoxy-2[4-(4-fluorobenzoyl]-1-piperazinyl}pyrimidine
  chlorohydrate,
2-[4-(2-thiazoyicarbonyl )-1-piperazinyl]-4-
  methoxypyrimidine,
2-[4-(2-aminobenzoyl)-1-piperazinyl]-4-
  methoxypyrimidine,
2-[4-(2-aminobenzoyl)-1-piperazinyl]-4-
  methoxypyrimidine chlorohydrate,
2-[4-(3-fluoro-2-thieylcarbonyl)-1-piperazinyl]-4-
  methoxypyrimidine,
2-[4-(3-fluoro -2-thieylcarbonyl)-1-piperazinyl]-4-
  methoxypyrimidine chlorohydrate,
2-[4-(4-methoxy-2-pyrimidinyl)-l1-piperazinylcarbonyl]
  benzoic acid,
2-[4-(2-acetoxybenzoyl)-1-piperazinyl]-4-
  methoxypyrimidine,
2-[4-(2-hydroxybenzoyl)-1-piperazinyl]-4-
  methoxypyrimidine, sodium 2-[4-(4-methoxy-2-
  pyrimidinyl)-1-piperazinylcarbonyl]benzoate,
2-[4-(2-hydroxybenzoyl)-1-piperazinyl]-4-
  methoxypyrimidine hydrochlorate,
4-methoxy-2-[4-(2-methoxybenzoyl)-1-piperazinyl]-4-
  methoxypyrimidine, and
4-ethoxy-2[4-(2-pyridylcarbonyl]-1-
  piperazinyl}pyrimidine.

10. Procedure for the preparation of a compound of formula (1) as defined in claim 1, wherein X represents an atom of oxygen, which comprises reacting a chloropyrimidine of formula (III)

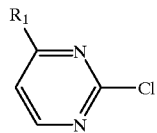

where $R_1$ has the meaning defined in claim 1, with a piperazine of formula (IV)

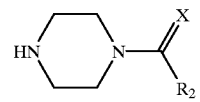

where $R_2$ has the meaning defined in claim 1 and X represents an oxygen atom.

11. Procedure for the preparation of a compound of formula (I) as defined in claim 1, wherein X represents an atom of oxygen, which comprises reacting an amine of formula (V)

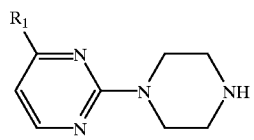

where $R_1$ has the meaning defined in claim 1, with a carboxylic acid of formula $R_2COOH$ (Vl) or with a salt of said acid, in which $R_2$ has the meaning defined in claim 1.

12. Procedure for the preparation of compound of formula (I) as defined in claim 1 wherein X represents an oxygen atom, which comprises reacting an amine of formula (V)

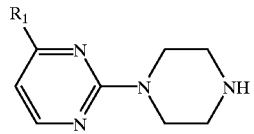

where $R_1$ has the meaning defined in claim 1 with a derivative reagent $R_2COY$ (VII), in which $R_2$ has the meaning defined in claim 1 and Y represents a halogen atom, an azide group, a 1-imidazolyl group, a $O-CO-R_4$ group, where $R_4$ represents an alkyl radical of 1 to 6 atoms of carbon or an aryl radical, optionally substituted with one or several halogen atoms, or an $OR_5$ group where $R_5$ represents an aromatic group or one or two rings substituted with one or several halogen atoms or nitro radicals, or N-succinimide.

13. Procedure for the preparation of a compound of formula (I) as defined in claim 1 wherein X represents a sulfur atom, which comprises reacting a compound of formula (I) in which X represents an oxygen atom, with Lawesson's reagent, (2,4-bis(4-methoxyphenyl)-1,3,2,4-dithiadiphosphaethano-2,4-disulphuride), or with phosphorous pentasulphide.

14. Procedure for the preparation of the physiologically acceptable salts of the compounds of formula (I), as defined in claim 1, which comprises reacting a compound of formula (I) with a mineral acid or an organic acid in an appropriate solvent.

15. A pharmaceutical composition comprising a pharmaceutically acceptable excipient, and at least one compound of formula (I) as defined in claim 1 or one of its physiologically acceptable salts.

16. A method for inducing sleep in a mammal comprising administering an effective amount of an acyl-pyrimidine of formula (I) as defined in claim 1 or a physiologically acceptable salt thereof to the mammal in need thereof.

17. A method for anaesthetizing a mammal comprising administering an effective amount of an acyl-pyrimidine of formula (I) as defined in claim 1 or a physiologically acceptable salt thereof to the mammal in need thereof.

18. A method for sedating a mammal comprising administering an effective amount of an acyl-pyrimidine of formula (I) as defined in claim 1 or a physiologically acceptable salt thereof to the mammal in need thereof.

19. A method for relaxing muscles in a mammal comprising administering an effective amount of an acyl-pyrimidine of formula (I) as defined in claim 1 or a physiologically acceptable salt thereof to the mammal in need thereof.

20. A method for relieving pain in a mammal comprising administering an effective amount of an acyl-pyrimidine of formula (I) as defined in claim 1 or a physiologically acceptable salt thereof to the mammal in need thereof.

21. A method for treating a migraine in a mammal comprising administering an effective amount of an acyl-pyrimidine of formula (I) as defined in claim 1 or a physiologically acceptable salt thereof to the mammal in need thereof.

22. A method for preventing convulsions in a mammal at risk for having convulsions comprising administering an effective amount of an acyl-pyrimidine of formula (I) as defined in claim 1 or a physiologically acceptable salt thereof to the mammal in need thereof.

23. A method for treating convulsions in a mammal comprising administering an effective amount of an acyl-pyrimidine of formula (I) as defined in claim 1 or a physiologically acceptable salt thereof to the mammal in need thereof.

* * * * *